United States Patent
Lee et al.

(10) Patent No.: US 11,124,772 B2
(45) Date of Patent: Sep. 21, 2021

(54) METHOD TO ALTER CHINESE HAMSTER OVARY CELL LINE STABILITY

(71) Applicants: Kelvin Lee, Newark, DE (US); Xiaolin Zhang, Iselin, NJ (US)

(72) Inventors: Kelvin Lee, Newark, DE (US); Xiaolin Zhang, Iselin, NJ (US)

(73) Assignee: University of Delaware, Newark, DE (US)

( * ) Notice: Subject to any disclaimer, the term of this patent is extended or adjusted under 35 U.S.C. 154(b) by 266 days.

(21) Appl. No.: 16/372,932

(22) Filed: Apr. 2, 2019

(65) Prior Publication Data
US 2019/0300859 A1   Oct. 3, 2019

Related U.S. Application Data

(60) Provisional application No. 62/651,317, filed on Apr. 2, 2018.

(51) Int. Cl.
| | |
|---|---|
| *C12N 5/071* | (2010.01) |
| *C12N 9/00* | (2006.01) |
| *C12N 9/88* | (2006.01) |
| *C12N 15/85* | (2006.01) |
| *C07K 14/47* | (2006.01) |

(52) U.S. Cl.
CPC ............ *C12N 5/0682* (2013.01); *C12N 9/88* (2013.01); *C12N 9/93* (2013.01); *C12Y 402/99* (2013.01); *C12Y 605/01001* (2013.01); *C12N 2510/02* (2013.01); *C12N 2511/00* (2013.01)

(58) Field of Classification Search
None
See application file for complete search history.

(56) References Cited

PUBLICATIONS

Bryans et al. (Mutation Research 433 (1999) 53-58).*
Arentsen et al., "The effect of photochemical internalization of bleomycin in the treatment of urothelial carcinoma of the bladder: an in vitro study", Urol Oncol. 2014;32(1):49.e1-6.
Baik et al., "A framework to quantify karyotype variation associated with CHO production instability", Biotechnol Bioeng. 2016. pp. 1045-1053, doi: 10.1002/bit.26231.
Bandaranayake et al., "Recent advances in mammalian protein production", FEBS Lett. 2014;588(2):253-60.
Barnes et al., "Stability of protein production from recombinant mammalian cells", Biotechnol Bioeng. 2003;81(6):631-9.
Beckmann et al., "Effects of high passage cultivation on CHO cells: a global analysis", Appl Microbiol Biotechnol. 2012;94(3):659-71.
Biological approvals by year. U. S. Food and Drug Administration. 32 pages.
Chusainow et al., "A study of monoclonal antibody-producing CHO cell lines: what makes a stable high producer?", Biotechnol Bioeng. 2009;102(4):1182-96.

Deaven et al., "The chromosomes of CHO, an aneuploid Chinese hamster cell line: G-band, C-band, and autoradiographic analyses", Chromosoma. 1973;41(2):129-44.
Fell et al., "The Ku heterodimer: function in DNA repair and beyond", Mutat Res Rev Mutat Res. 2015;763:15-29.
Ferguson et al., "Genomic instability in human cancer: Molecular insights and opportunities for therapeutic attack and prevention through diet and nutrition", Semin Cancer Biol. 2015;35 Suppl:S5-24.
Hakem R., "DNA-damage repair; the good, the bad, and the ugly", Embo J. 2008;27(4):589-605.
Heller-Harrison et al., "Managing Cell Line Instability and Its Impact During Cell Line Development", www.biopharminternational.com/print/224283?page=full, Jun. 2, 2009. 9 pages.
Ivashkevich et al., "γH2AX foci as a measure of DNA damage: a computational approach to automatic analysis", Mutat Res. 2011;711(1-2):49-60.
Jamnikar et al., "Transcriptome study and identification of potential marker genes related to the stable expression of recombinant proteins in CHO clones", BMC Biotechnol. 2015;15:98.
Jin et al., "Double-strand break repair by Ku70 requires heterodimerization with Ku80 and DNA binding functions", EMBO J. 1997;16(22):6874-85.
Khanna et al., "DNA double-strand breaks: signaling, repair and the cancer connection", Nat Genet. 2001;27(3):247-54.
Kim et al., "A mechanistic understanding of production instability in CHO cell lines expressing recombinant monoclonal antibodies", Biotechnol Bioeng. 2011;108(10):2434-46.
Martin et al., "New record of biologics sales in 2015 exceeding the USD 150 bln threshold", La Merie Publishing. Mar. 14, 2016.
Mladenov et al., "The complexity of double-strand break ends is a factor in the repair pathway choice", Radiat Res. 2009;171(4):397-404.
Moritz et al., "CMV promoter mutants with a reduced propensity to productivity loss in CHO cells", Sci Rep. 2015;5:16952.
Mutskov et al., "Silencing of transgene transcription precedes methylation of promoter DNA and histone H3 lysine 9", EMBO J. 2004;23(1):138-49.
Negrini et al., "Genomic instability—an evolving hallmark of cancer", Nat Rev Mol Cell Biol. 2010;11(3):220-8.

(Continued)

*Primary Examiner* — Suzanne M Noakes
*Assistant Examiner* — Jae W Lee
(74) *Attorney, Agent, or Firm* — RatnerPrestia

(57) ABSTRACT

The present invention provides a recombinant eukaryotic cell expressing one or more heterologous double strand break (DSB) repair proteins in an amount effective for enhancing DSB repair in the cell. The recombinant eukaryotic cell may express a recombinant product of interest. Also provided are methods for enhancing double strand break (DSB) repair in eukaryotic cells, establishing host cells for production of a recombinant product of interest, producing a recombinant product of interest, improving production of a recombinant product of interest by eukaryotic cells, and/or investigating suitability of eukaryotic cells as host cells for producing a recombinant product of interest.

18 Claims, 6 Drawing Sheets
Specification includes a Sequence Listing.

(56) References Cited

PUBLICATIONS

Parades et al., "Unstable expression of recombinant antibody during long-term culture of CHO cells is accompanied by histone H3 hypoacetylation", Biotechnol Lett. 2013;35(7):987-93.
Richardson et al., "Frequent chromosomal translocations induced by DNA double-strand breaks", Nature. 2000;405(6787):697-700.
Ritter et al., "Fam60A plays a role for production stabilities of recombinant CHO cell lines", Biotechnol Bioeng. 2016;9999:1-4.
Schär P., "Spontaneous DNA damage, genome instability, and cancer—when DNA replication escapes control", Cell. 2001;104(3):329-32.
Tounekti et al., "The ratio of single- to double-strand DNA breaks and their absolute values determine cell death pathway", Br J Cancer. 2001;84(9):1272-9.
Veith et al., "Mechanisms underlying epigenetic and transcriptional heterogeneity in Chinese hamster ovary (CHO) cell lines", BMC Biotechnol. 2016;16:6.
Worton et al., "Chromosome stability in CHO cells", Somatic Cell Genet. 1977;3(1):27-45.
Wurm et al., "First CHO genome", Nat Biotechnol. 2011;29(8):718-20.
Yang et al., "DNA methylation contributes to loss in productivity of monoclonal antibody-producing CHO cell lines", J Biotechnol. 2010;147(3-4):180-5.

\* cited by examiner

A n=333; n=129; n=214
p-value < 2.2e-16
p-value: 0.20

B

C

A

- Induce same amount of DSBs by BL
- Repair DSBs by cells

B

A

B

C

D

ND STATES 11,124,772 B2

METHOD TO ALTER CHINESE HAMSTER OVARY CELL LINE STABILITY

CROSS-REFERENCE TO RELATED APPLICATION

This application claims priority to U.S. Provisional Application No. 62/651,317, filed Apr. 2, 2018, the contents of which are incorporated herein by reference in their entireties for all purposes.

REFERENCE TO U.S. GOVERNMENT SUPPORT

This invention was made with government support under Grant Nos. 1412365 and 1539359 by the National Science Foundation. The United States has certain rights in the invention.

FIELD OF THE INVENTION

The invention relates generally to improvement of stability of host cells for producing recombinant proteins.

BACKGROUND OF THE INVENTION

The biopharmaceutical sector is the fastest growing part of pharmaceutical industry. With an annual growth rate of 9.2%, global annual sales of recombinant therapeutic proteins reached $154 billion in 2015 and will continue to grow. The strong demand from the market, combined with an increasing number of innovative therapeutic proteins approved by US Food and Drug Administration (FDA), provides significant drivers to ensure stable, high productivity and product quality in existing and newly created cell lines used to manufacture these molecules.

Chinese hamster ovary (CHO) cells are the most important cell lines for commercial manufacturing of therapeutic proteins, and produce more than $100 billion per year of products. A key factor that resulted in the broad use of CHO as a platform is the immense adaptive ability of the cells that allows growth at high cell density in serum-free suspension culture, and also allows selection of clones with diverse phenotypes including high productivity as well as clones expressing products with desired product characteristics. The exceptional adaptability of CHO cells arises from an inherent genome instability—DNA sequence changes and chromosomal rearrangements occur frequently during cell culture. However, this "unstable genome" also has an undesirable consequence when it comes to selected clones with desired properties: there is the chance for cells to reduce the copy number or alter the expression of integrated transgenes, which in turn manifests as an inability to maintain high productivity or product quality over relevant time periods for commercial application: ~60 days in culture. This production instability remains a key concern in commercial manufacturing processes.

Beyond genome instability, another often-reported cause of production instability is a decrease in transgene transcripts, mainly due to the epigenetic silencing via promoter methylation and histone modifications. So far, two reports have targeted this mechanism and increased production stability by using CMV promoter mutants to prevent promoter methylation, or by deleting the gene Fam60A which acts presumably to decrease histone deacetylation. However, although epigenetic transcriptional silencing was associated with production instability in some cell lines, a reduction in the transgene copy number due to genome instability was the predominant cause of production instability in a majority of cell lines. The inability to maintain genome integrity will negatively affect production stability in most, if not all, production cell lines during long-term culture. Yet, no study has been able to control production stability by addressing the genome instability problem in CHO cells.

Genome instability is a common feature of most cancers, and can arise from defects in DNA damage repair. Of all types of DNA damages, the most toxic is double strand break (DSB). Two distinct and complementary DSB repair pathways (NHEJ and HDR) have evolved to protect the genome from deleterious effect of DSBs. Non-homologous end joining (NHEJ) pathway ligates the two ends of broken DNA together with limited trimming of DNA ends, but is intrinsically error-prone. In contrast, the homology directed repair (HDR) pathway requires a homologous sequence to faithfully restore the original sequence of the broken DNA. Many genes are involved in the two pathways, and mutations in these genes could result in DNA sequence alternations and chromosomal rearrangements, which often contribute to carcinogenesis. The inherent genome instability of CHO cells, particularly the frequent chromosomal rearrangements, is also possibly attributed to a deficient DSB repair caused by mutations in DSB repair genes. Given that Chinese hamster (CH) cells, from which CHO cells were originally derived, have a stable genome and thus a functional DSB repair, expressing functional (CH) DSB repair genes in CHO cells could be a potential way to rescue the DSB repair system and improve the genome stability.

There remains a need for a method to improve stability of host cells for producing recombinant proteins.

SUMMARY OF THE INVENTION

The present invention relates to enhancement of double strand break (DSB) repair in and stability of eukaryotic cells and the use such eukaryotic cells to produce products of interest.

A recombinant eukaryotic cell is provided. The recombinant eukaryotic cell expresses a heterologous double strand break (DSB) repair protein in an amount effective for enhancing DSB repair in the cell. The heterologous DSB repair protein may be expressed in an amount effective for enhancing stability of the cell for at least 1 month. The heterologous DSB repair protein may be selected from the group consisting of DNA ligase IV (LIG4), x-ray repair cross complementing 6 (XRCC6), partner and localizer of BRCA2 (PALB2), and PARP1 binding protein which is encoded by the PARPBP gene (PARI). The heterologous DSB repair protein may be LIG4 or XRCC6. The heterologous DSB repair protein may be expressed transiently or stably.

The recombinant eukaryotic cell may be a mammalian cell. The mammalian cell may be selected from the group consisting of a rodent cell, a mouse cell and a Chinese hamster cell. The mammalian cell may be a Chinese hamster ovary (CHO) cell.

The heterologous DSB repair protein may be from the Chinese hamster. The heterologous DSB repair protein may comprise an amino acid sequence at least 70% identical to the amino acid sequence of SEQ ID No: 1 or 2.

The heterologous DSB repair protein may be from a Chinese hamster ovary cell. The heterologous DSB repair protein may comprise an amino acid sequence at least 70% identical to the amino acid sequence of SEQ ID No: 3 or 4.

The recombinant eukaryotic cell may comprise a heterologous DSB repair gene encoding the heterologous DSB repair protein. The heterologous DSB repair gene may comprise a nucleic acid sequence at least 70% identical to the nucleic acid sequence of SEQ ID No: 5, 6, 7 or 8. The heterologous DSB repair gene may be integrated into the genome of the recombinant eukaryotic cell.

The recombinant eukaryotic cell may comprise a heterologous nucleic acid sequence encoding a recombinant product of interest and expressing the recombinant product of interest. The recombinant product of interest may be a protein or a polypeptide. The protein may be a monoclonal antibody. The heterologous nucleic acid sequence encoding the recombinant product of interest may be integrated into the genome of the recombinant eukaryotic cell. The recombinant product of interest may be a secreted embryonic alkaline phosphate (SEAP).

The recombinant eukaryotic cell may further comprise a heterologous nucleic acid sequence encoding a selection marker integrated into the genome of the recombinant eukaryotic cell.

A method for enhancing double strand break (DSB) repair in eukaryotic cells (enhancement method) is provided. The method comprises expressing an effective amount of a heterologous DSB repair protein in the eukaryotic cells. The method may further comprise enhancing stability of the eukaryotic cells over time. The method may further comprise introducing into the eukaryotic cells a heterologous nucleic acid gene encoding the heterologous DSB repair protein. The heterologous nucleic acid sequence encoding the heterologous DSB repair protein may be introduced into the eukaryotic cells by overexpression, transgene expression, gene knock-in, gene activation, transcription activation, translation activation, gene mutation or a combination thereof.

A method for establishing host cells for production of a recombinant product of interest (establishment method) is provided. The method comprises (a) expressing a heterologous double strand break (DSB) repair protein in the eukaryotic cells; (b) determining DSB repair in the eukaryotic cells of step (a); and (c) isolating eukaryotic cells in which the DSB repair is enhanced as host cells. The method may further comprise editing the genome of the host cells to improve DSB repair in the host cells. Host cells established according to this method are provided.

A method for producing a recombinant product of interest (production method) is provided. The method comprises (a) growing eukaryotic cells in a culture medium, wherein the recombinant eukaryotic cells comprise a heterologous nucleic acid sequence encoding a recombinant product of interest; (b) expressing a heterologous double strand break (DSB) repair protein in the eukaryotic cells; and (c) expressing the recombinant product of interest by the eukaryotic cells. The average productivity of the recombinant product of interest by the eukaryotic cells may drop less than 30% over a period of at least 8 weeks. The eukaryotic cells may retain at least 70% of the copy number of the heterologous nucleic acid sequence encoding the recombinant product of interest over a period of at least 8 weeks. The method may further comprise editing the genome of the eukaryotic cells to improve DSB repair in the eukaryotic cells. The method may further comprise expressing a selection maker by the eukaryotic cells, which may further comprise a heterologous nucleic acid sequence encoding the selection marker, and the heterologous nucleic acid sequence encoding the recombinant product of interest and the heterologous nucleic acid sequence encoding the selection marker may be integrated into the genome of the eukaryotic cells. The method may further comprise growing the eukaryotic cells under a condition that induces DNA damage. The recombinant product of interest may be a protein or a polypeptide. The protein may be a monoclonal antibody.

A method of improving production of a recombinant product of interest by eukaryotic cells (improvement method) is provided. The eukaryotic cells comprise a heterologous nucleic acid sequence encoding the recombinant product of interest and produce the recombinant product of interest. The method comprises expressing a heterologous double strand break (DSB) repair protein by the recombinant eukaryotic cells. The method may further comprise enhancing DSB repair in the eukaryotic cells. The method may further comprise enhancing stability of the eukaryotic cells over time. The method may further comprise expressing a selection maker by the eukaryotic cells, which comprise a heterologous nucleic acid sequence encoding the selection marker. The heterologous nucleic acid sequence encoding the recombinant product of interest and the heterologous nucleic acid sequence encoding the selection marker may be integrated into the genome of the eukaryotic cells. The method may further comprise growing the eukaryotic cells under a condition that induces DNA damage. The recombinant product of interest may be a protein or a polypeptide. The protein may be a monoclonal antibody.

A method of investigating suitability of eukaryotic cells as host cells for producing a recombinant product of interest (investigation method) is provided. The eukaryotic cells comprise a heterologous nucleic acid sequence encoding the recombinant product of interest. The method comprises (a) expressing a heterologous double strand break (DSB) repair protein by the eukaryotic cells; and (b) determining DSB repair in the eukaryotic cells, wherein an improvement of the DSB repair indicates that the eukaryotic cells are suitable as host cells for producing a recombinant product of interest. The DSB repair protein may be selected from the group consisting of DNA ligase IV (LIG4), x-ray repair cross complementing 6 (XRCC6), partner and localizer of BRCA2 (PALB2), and PARP1 binding protein which is encoded by the PARPBP gene (PARI). The heterologous DSB repair protein may be LIG4 or XRCC6. Where the heterologous DSB repair protein is LIG4 or XRCC6, the method may further comprise quantifying the expression of the LIG4 or XRCC6 in the eukaryotic cells. The method may further comprise quantifying the expression of the recombinant product of interest by the eukaryotic cells. The method may further comprise identifying eukaryotic cells into whose genome the heterologous nucleic acid sequence encoding the recombinant product of interest is integrated. The method may further comprise identifying eukaryotic cells producing the recombinant product of interest in an amount greater than 100 mg per liter for recombinant eukaryotic cells, for example, grown in fed-batch culture. The method may further comprise expressing a selection maker by the eukaryotic cells, which may further comprise a heterologous nucleic acid sequence encoding the selection marker, and the heterologous nucleic acid sequence encoding the recombinant product of interest and the heterologous nucleic acid sequence encoding the selection marker may be integrated into the genome of the eukaryotic cells. The method may further comprise growing the eukaryotic cells under a condition that induces DNA damage. The recombinant product of interest may be a protein or a polypeptide. The protein may be a monoclonal antibody.

For the enhancement method, the establishment method, the production method, the improvement method, or the investigation method, the heterologous DSB repair protein may be expressed transiently or stably. The eukaryotic cells may be mammalian cells. The mammalian cells may be selected from the group consisting of rodent cells, mouse cells and Chinese hamster cells. The mammalian cells may be CHO cells. The heterologous DSB repair protein may be from a Chinese hamster (CH) cell or a Chinese hamster ovary (CHO) cell. The heterologous DSB repair protein may comprise an amino acid sequence at least 70% identical to the amino acid sequence of SEQ ID No: 1, 2, 3 or 4. The eukaryotic cell may comprise a heterologous DSB repair gene encoding the heterologous DSB repair protein. The heterologous DSB repair gene may comprise a nucleic acid sequence at least 70% identical to the nucleic acid sequence of SEQ ID No: 5, 6, 7 or 8. The heterologous DSB repair gene may be integrated into the genome of the eukaryotic cell.

DETAILED DESCRIPTION OF THE INVENTION

Figure 1:
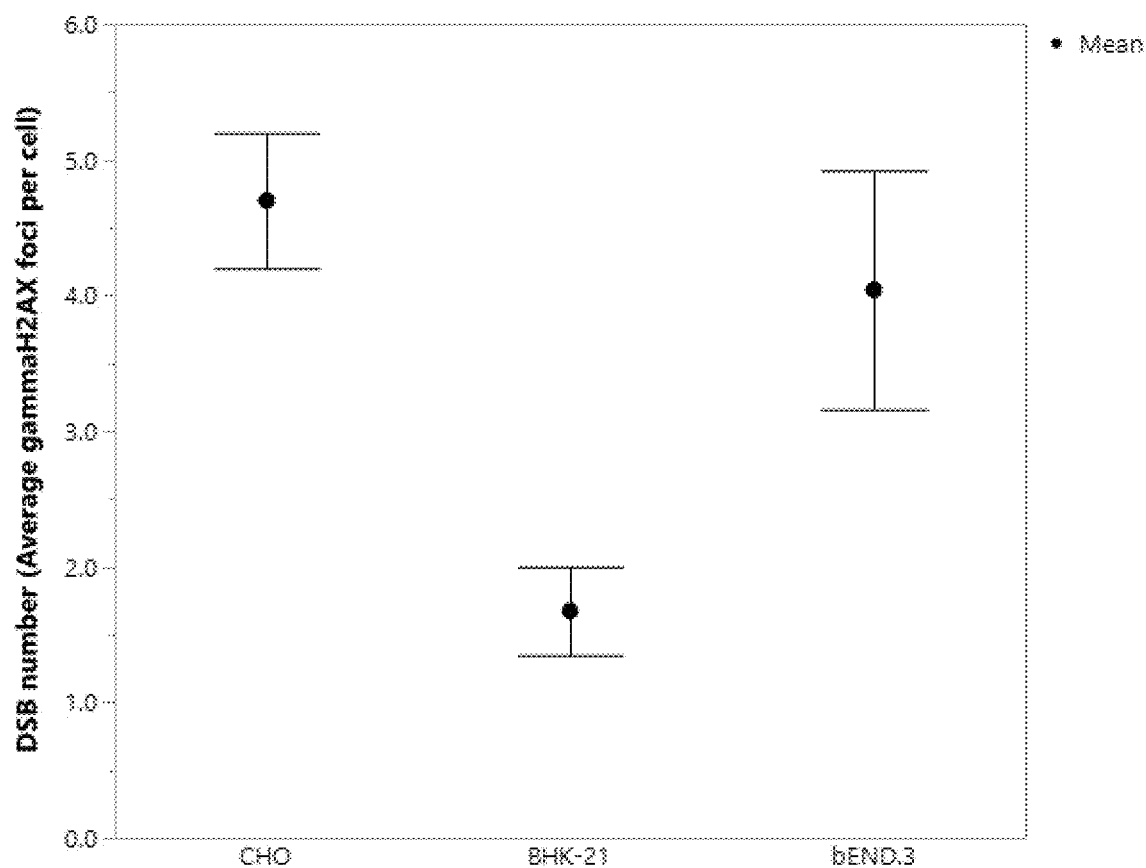
FIG. 1 shows (A) endogenous DSB numbers in CHO-K1, BHK-21 and bEnd.3 cells, and remaining DSB numbers after one-hour treatment with 10 (B) or 50 μg/mL (C) bleomycin. Each error bar is constructed using a 95% confidence interval of the mean. The letter n represents the number of cells used for counting γH2AX foci. The p-value was obtained by the Student's t-test. On the scatter plot, the 95% confidence interval is drawn for the mean DSB number at the given time point.
Figure 1:
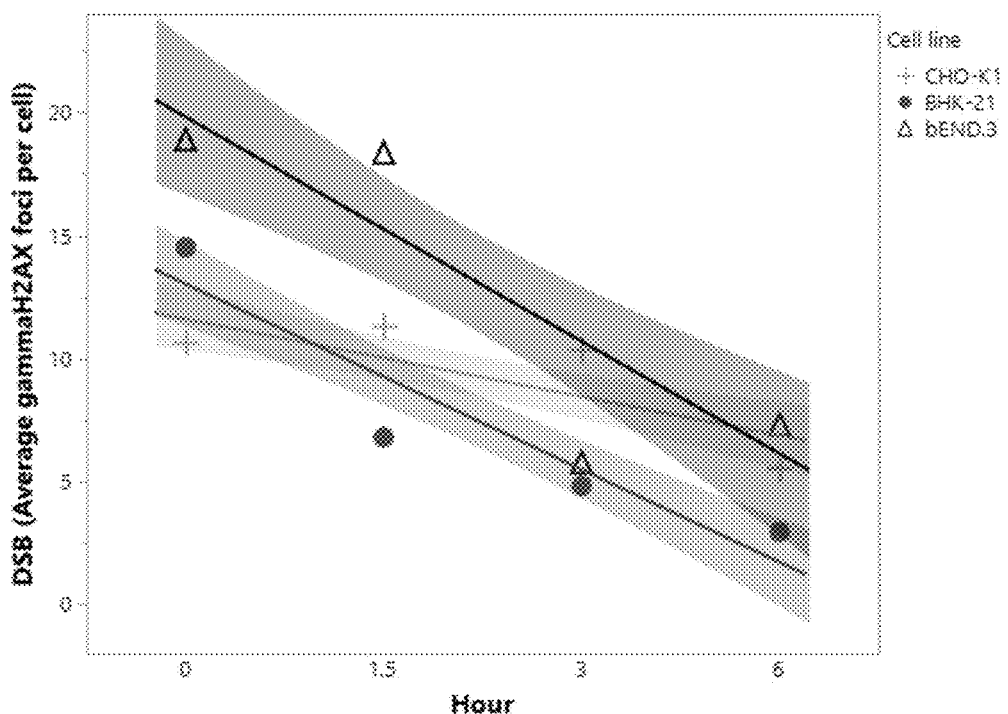
Figure 1:
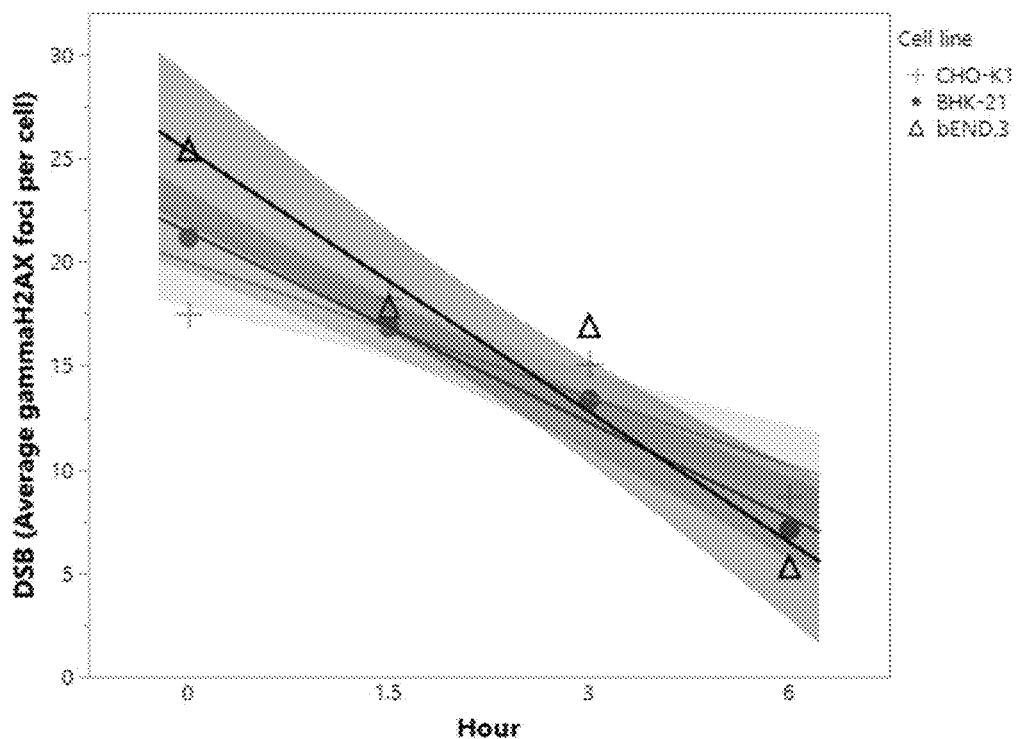

The present invention relates to alteration of stability of host cells for producing recombinant proteins. The invention is made based on the surprising discovery when double strand break (DSB) repair and genome stability in Chinese hamster ovary (CHO) cells were investigated. The inventors have discovered that DSB repair in CHO cells is deficient, but heterologous expression of DSB repair genes from Chinese hamster (CH) cells in CHO cells can improve DSB repair dramatically in the CHO cells. Enhancement of DSB repair in cells increases genome and production stabilities of the cells.

The term "polypeptide" used herein refers to a polymer of amino acid residues with no limitation with respect to the minimum length of the polymer. For example, the polypeptide may have at least 20 amino acids. A polypeptide may be modified by, for example, glycosylation and/or phosphorylation.

The term "protein" used herein refers to a biological molecule comprising one or more polypeptides. The protein may be an antibody, or a variant, derivative, analog, or fragment thereof, which specifically binds to an antigen of interest. The antibody may be a polyclonal antibody, a monoclonal antibody, a chimeric antibody, CDR-grafted antibody or humanized antibody.

The term "polynucleotide" used herein refers to a polymer of nucleotide residues with no limitation with respect to the minimum length of the polymer. For example, the polynucleotide may have at least 60 nucleotides. The polynucleotide may be a DNA, cDNA or RNA molecule, or a combination thereof.

The term "variant" of a protein, polypeptide or polynucleotide used herein refers to a respective protein, polypeptide or polynucleotide having an amino acid or nucleic acid sequence that is the same as the amino acid or nucleic acid sequence of the original protein, polypeptide or polynucleotide except having at least one amino acid or nucleic acid modified, for example, deleted, inserted, or replaced, respectively. A variant of a protein, polypeptide or polynucleotide may have an amino acid or nucleic acid sequence at least about 80%, 90%, 95%, or 99%, preferably at least about 90%, more preferably at least about 95%, identical to the amino acid sequence or nucleic acid of the original protein, polypeptide or polynucleotide.

A recombinant eukaryotic cell is provided. The recombinant eukaryotic cell expresses one or more heterologous double strand break (DSB) repair proteins in an amount effective for enhancing DSB repair in the cell. The DSB repair protein may be expressed in an amount effective for enhancing stability of the cell over time.

The term "double strand break (DSB) repair" used herein refers to the molecular mechanism inside cells wherein the cell is able to repair a break in both strands of the DNA using either of two mechanisms known as homologous recombination or non-homologous end-joining recombination. DSB repair in a cell or cells may be evaluated by using an assay called the γ-H2AX assay. For example, the phosphorylated histone H2AX may be a tool to monitor DNA double strand breaks because it is known that the Ser 139 residue in H2AX, a variant of the core histone H2A family, becomes phosphorylated immediately after the introduction of DNA damage. This phosphorylated version of H2AX is known as γ-H2AX and may be assayed with an antibody that binds to γ-H2AX and measured. The greater the amount of γ-H2AX is observed, the greater the number of DSBs may be present.

The term "stability" as used herein refers to no significant change (e.g., no more than 1%, 2%, 5%, 10%, 15%, 18%, 20%, 25%, 30%, 35% or 40%) in one or more characteristics of a cell over a period. The period may be at least 1, 2, 3, 4, 5, 6 or 7 weeks, 1 month, or 1, 2, 5, 10, 20, 30, 40, 50, or 60 population doublings of the cell culture. The period may be no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture. The period may be 1-10, 1-30, 1-60 days from the start of cultivation of the cells. Examples of the characteristics of a cell include growth rate or genome of the cell, expression of endogenous proteins or growth factors by the cell, a heterologous nucleic acid sequence, whether integrated into the genome of the cell, and production of a recombinant protein, for example, with a specific modification, by the cell.

In one embodiment, the eukaryotic cells may retain at least 30%, 35%, 40%, 45%, 50%, 55%, 60%, 65%, 70%, 75%, 80%, 85%, 90% or 95% of the copy number of the heterologous nucleic acid sequence encoding a heterologous DSB repair protein over a period of, for example, at least 1, 2, 3, 4, 5, 6 or 7 weeks, 1 month, or 1, 2, 5, 10, 20, 30, 40, 50, or 60 population doublings of the cell culture, and/or no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture. The nucleic acid sequence encoding the heterologous DSB repair protein may be integrated into the genome of the cell.

In another embodiment, the eukaryotic cells may retain at least 30%, 35%, 40%, 45%, 50%, 55%, 60%, 65%, 70%, 75%, 80%, 85%, 90% or 95% of the copy number of the heterologous nucleic acid sequence encoding a recombinant product of interest over a period of, for example, at least 1, 2, 3, 4, 5, 6 or 7 weeks, 1 month, or 1, 2, 5, 10, 20, 30, 40, 50, or 60 population doublings of the cell culture, and/or no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture The nucleic acid sequence encoding the recombinant product of interest may be integrated into the genome of the cell.

The term "productivity" as used herein refers to the amount of a recombinant product of interest produced by eukaryotic cells grown in a culture medium over time. The productivity may be expressed in units of grams per liter for a fed-batch culture where cells are cultivated in medium in a vessel and nutrients are periodically added to the vessel with the purpose of extending the duration of the culture. The purpose of the periodic addition of nutrients to the vessel may also be to increase the amount of recombinant protein produced. In a continuous culture, nutrients are continuously added to cells grown in a vessel and waste products are continuously removed from the vessel. In a continuous culture, the productivity of the cells may be expressed as a volumetric productivity in units of grams per liter per day. The recombinant product of interest may be expressed by the cells and remain inside the cells or secreted by the cells into the culture medium. The productivity of a recombinant product of interest by eukaryotic cells may drop over time. The production of the recombinant product of interest is deemed stable production if no more than 1%, 2%, 5%, 10%, 15%, 18%, 20%, 25%, 30%, 35% or 40% of the productivity of a recombinant product of interest, for example, a heterologous recombinant protein (e.g., antibody), drops in eukaryotic cells over a period. The period may be at least 1, 2, 3, 4, 5, 6 or 7 weeks, 1 month, or 1, 2, 5, 10, 20, 30, 40, 50, or 60 population doublings of the cell culture. The period may be no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture. The period may be 1-10, 1-30, or 1-60 days from the start of cultivation of the cells.

The term "an effective amount" used herein refers to an amount of the heterologous double strand break (DSB) repair protein(s) expressed in the cell required to achieve a stated goal (e.g., enhancement of DSB repair in the cell or enhancement of stability of the cell). The effective amount of the heterologous DSB repair protein(s) may vary depending upon the stated goals, the biological state of the cell and the environment surrounding the cell.

The recombinant eukaryotic cell may be a mammalian cell. The mammalian cell may be a rodent cell, a mouse cell and a Chinese hamster cell. The mammalian cell may be a CHO cell.

The heterologous DSB repair protein may be expressed transiently or stably. In one embodiment, the heterologous DSB repair protein may be expressed stably.

The heterologous DSB repair protein may be from any cell, in which DSB repair occurs naturally, other than the eukaryotic cell from which the recombinant eukaryotic cell is prepared. The heterologous DSB repair protein may be identical to an endogenous protein involved in DSB repair in a cell other than the eukaryotic cell from which the recombinant eukaryotic cell is prepared. The heterologous DSB repair protein may be identical to an endogenous DSB repair protein from a cell other than the eukaryotic cell from which the recombinant eukaryotic cell is prepare, or a variant thereof. The heterologous DSB repair protein may be identical to an endogenous DSB repair protein in a Chinese hamster (CH) cell, or a variant thereof. The heterologous DSB repair protein may be identical to an endogenous DSB repair protein in a Chinese hamster ovary (CHO) cell line, or a variant thereof. The heterologous DSB repair protein may be selected from the group consisting of DNA ligase IV (LIG4), x-ray repair cross complementing 6 (XRCC6), partner and localizer of BRCA2 (PALB2), and PARP1 binding protein which is encoded by the PARPBP gene (PARI). In some embodiments, the DSB repair protein may be LIG4 or XRCC6.

The heterologous DSB repair protein may comprise an amino acid sequence at least 70%, 75%, 80%, 85%, 90%, 95%, 96%, 97%, 98% or 99% identical to the amino acid sequence of SEQ ID No: 1, 2, 3 or 4. The heterologous DSB repair protein may comprise the amino acid sequence of SEQ ID No: 1, 2, 3 or 4. The heterologous DSB repair protein may consist of the amino acid sequence of SEQ ID No: 1, 2, 3 or 4.

The recombinant eukaryotic cell may comprise a heterologous DSB repair gene encoding the heterologous DSB repair protein. The heterologous DSB repair gene may encode LIG4, XRCC6, PALB2 or PARI. In some embodiments, the heterologous DSB repair gene may encode LIG4 or XRCC6. The heterologous DSB repair gene may comprise a nucleic acid sequence at least 70%, 75%, 80%, 85%, 90%, 95%, 96%, 97%, 98% or 99% identical to the nucleic acid sequence of SEQ ID No: 5, 6, 7 or 8. The heterologous DSB repair gene may comprise the nucleic acid sequence of SEQ ID No: 5, 6, 7 or 8. The heterologous DSB repair gene may consist of the nucleic acid sequence of SEQ ID No: 5, 6, 7 or 8. The heterologous DSB repair gene may be integrated into the genome of the recombinant eukaryotic cell.

The recombinant eukaryotic cell may comprise a heterologous nucleic acid sequence encoding a recombinant product of interest and express the recombinant product of interest. The heterologous nucleic acid sequence encoding the recombinant product of interest may be integrated into the genome of the recombinant eukaryotic cell.

The recombinant product of interest may be a protein, polypeptide, or antibody. For example, the recombinant product of interest may be secreted embryonic alkaline phosphate (SEAP). The recombinant product of interest may be an antibody, for example, a polyclonal antibody, a monoclonal antibody, a chimeric antibody, CDR-grafted antibody or humanized antibody. In one embodiment, the recombinant product of interest may be a monoclonal antibody.

The recombinant eukaryotic cell may further comprise a heterologous nucleic acid sequence encoding a selection marker. The heterologous nucleic acid sequence encoding the selection marker may be integrated into the genome of the recombinant eukaryotic cell.

A method for enhancing double strand break (DSB) repair in eukaryotic cells (enhancement method) is provided. The method comprises expressing an effective amount of a heterologous DSB repair protein in the eukaryotic cells. The eukaryotic cells may be mammalian cells. The mammalian cells may be selected from the group consisting of rodent cells, mouse cells and Chinese hamster cells. The mammalian cells may be CHO cells. The heterologous DSB repair protein may be from a Chinese hamster (CH) cell. The heterologous DSB repair protein may be from a Chinese hamster ovary (CHO) cell.

The enhancement method may further comprise enhancing stability of the eukaryotic cells over time. The heterologous DSB repair protein may be LIG4, XRCC6, PALB2 or PARI, preferably, LIG4 or XRCC6. The heterologous DSB repair protein may comprise an amino acid sequence at least 70%, 75%, 80%, 85%, 90%, 95%, 96%, 97%/0, 98%$^0$ or 99% identical to the amino acid sequence of SEQ ID No: 1, 2, 3 or 4. The heterologous DSB repair protein may comprise the amino acid sequence of SEQ ID No: 1, 2, 3 or 4. The heterologous DSB repair protein may consist of the amino acid sequence of SEQ ID No: 1, 2, 3 or 4.

The enhancement method may further comprise introducing into the eukaryotic cells a heterologous nucleic acid gene encoding the heterologous DSB repair protein. The heterologous nucleic acid sequence encoding the heterologous DSB repair protein may be introduced into the eukaryotic cells by overexpression, transgene expression, gene knock-in, gene activation, transcription activation, translation activation, gene mutation or a combination thereof. The heterologous DSB repair gene may encode LIG4, XRCC6, PALB2 or PARI, preferably, LIG4 or XRCC6. The heterologous DSB repair gene may comprise a nucleic acid sequence at least 70%, 75%, 80%, 85%, 90%, 95%, 96%, 97%, 98%0 or 99% identical to the nucleic acid sequence of SEQ ID No: 5, 6, 7 or 8. The heterologous DSB repair gene may comprise the nucleic acid sequence of SEQ ID No: 5, 6, 7 or 8. The heterologous DSB repair gene may consist of the nucleic acid sequence of SEQ ID No: 5, 6, 7 or 8. The heterologous DSB repair gene may be integrated into the genome of the recombinant eukaryotic cell.

A method for establishing host cells for production of a recombinant product of interest (establishment method) is provided. The method comprises expressing a heterologous double strand break (DSB) repair protein in the eukaryotic cells; determining DSB repair in the eukaryotic cells of step (a); and isolating eukaryotic cells in which the DSB repair is enhanced as host cells. The method may further comprise editing the genome of the host cells to improve DSB repair in the host cells.

According to the establishment method, the heterologous DSB repair protein may be expressed transiently or stably, preferably stably, in the eukaryotic cells. The eukaryotic cells may be mammalian cells. The mammalian cells may be selected from the group consisting of rodent cells, mouse cells and Chinese hamster cells. The mammalian cells may be CHO cells. The heterologous DSB repair protein may be from a Chinese hamster (CH) cell. The heterologous DSB repair protein may be from a Chinese hamster ovary (CHO) cell. The heterologous DSB repair protein may be LIG4, XRCC6, PALB2 or PARI, preferably, LIG4 or XRCC6. The heterologous DSB repair protein may comprise an amino acid sequence at least 70%, 75%, 80%, 85%, 90%, 95%, 96%, 97%, 98% or 99% identical to the amino acid sequence of SEQ ID No: 1, 2, 3 or 4. The heterologous DSB repair protein may comprise the amino acid sequence of SEQ ID No: 1, 2, 3 or 4. The heterologous DSB repair protein may consist of the amino acid sequence of SEQ ID No: 1, 2, 3 or 4. The eukaryotic cells may comprise a heterologous nucleic acid sequence encoding the heterologous DSB repair protein. The heterologous DSB repair gene may be integrated into the genome of the eukaryotic cell. The heterologous DSB repair gene may encode LIG4, XRCC6, PALB2 or PARI, preferably, LIG4 or XRCC6. The heterologous DSB repair gene may comprise a nucleic acid sequence at least 70%, 75%, 80%, 85%, 90%, 95%, 96%, 97%, 98% or 99% identical to the nucleic acid sequence of SEQ ID No: 5, 6, 7 or 8. The heterologous DSB repair gene may comprise the nucleic acid sequence of SEQ ID No: 5, 6, 7 or 8. The heterologous DSB repair gene may consist of the nucleic acid sequence of SEQ ID No: 5, 6, 7 or 8.

According to the establishment method, the eukaryotic cells may comprise a heterologous nucleic acid sequence encoding a recombinant product of interest and express the recombinant product of interest. The heterologous nucleic acid sequence encoding the recombinant product of interest may be integrated into the genome of the recombinant eukaryotic cell. The recombinant product of interest may be a protein or polypeptide. For example, the recombinant product of interest may be secreted embryonic alkaline phosphate (SEAP). The recombinant product of interest may be an antibody, for example, a polyclonal antibody, a monoclonal antibody, a chimeric antibody, CDR-grafted antibody or humanized antibody. In one embodiment, the recombinant product of interest may be a monoclonal antibody. The eukaryotic cells may further comprise a heterologous nucleic acid sequence encoding a selection marker. The heterologous nucleic acid sequence encoding the selection marker may be integrated into the genome of the recombinant eukaryotic cell.

For each method for establishing host cells for production of a recombinant product of interest, the established host cells are provided.

A method for producing a recombinant product of interest (production method) is provided. The method comprises growing eukaryotic cells in a culture medium. The eukaryotic cells comprise a heterologous nucleic acid sequence encoding a recombinant product of interest. The method further comprises expressing a heterologous double strand break (DSB) repair protein in the eukaryotic cells; and expressing the recombinant product of interest by the eukaryotic cells. The method may further comprise editing the genome of the eukaryotic cells to improve DSB repair in the eukaryotic cells. The method may further comprise growing the eukaryotic cells under a condition that induces DNA damage. A condition that induces DNA damage may involve the additional of chemicals to the culture expected to induce DNA damage and double-strand breaks. Another condition that induces DNA damage may involve the use of radiation exposure to the culture in a manner expected to induce DNA damage and double-strand breaks. Yet another condition that induces DNA damage may involve the application of a chemical selection pressure to cells to enable only those cells able to survive in the presence of relevant amounts of the chemical agent and which may induce DNA damage and double-strand breaks.

According to the production method, the heterologous DSB repair protein may be expressed transiently or stably, preferably stably, in the eukaryotic cells. The eukaryotic cells may be mammalian cells. The mammalian cells may be selected from the group consisting of rodent cells, mouse cells and Chinese hamster cells. The mammalian cells may be CHO cells. The heterologous DSB repair protein may be from a Chinese hamster (CH) cell. The heterologous DSB repair protein may be from a Chinese hamster ovary (CHO) cell. The heterologous DSB repair protein may be LIG4, XRCC6, PALB2 or PARI, preferably, LIG4 or XRCC6. The heterologous DSB repair protein may comprise an amino acid sequence at least 70%, 75%, 80%, 85%, 90%, 95%, 96%, 97%, 98% or 99% identical to the amino acid sequence of SEQ ID No: 1, 2, 3 or 4. The heterologous DSB repair protein may comprise the amino acid sequence of SEQ ID No: 1, 2, 3 or 4. The heterologous DSB repair protein may consist of the amino acid sequence of SEQ ID No: 1, 2, 3 or 4. The eukaryotic cells may comprise a heterologous nucleic acid sequence encoding the heterologous DSB repair protein. The heterologous DSB repair gene may be integrated into the genome of the eukaryotic cell. The heterologous DSB repair gene may encode LIG4, XRCC6, PALB2 or PARI, preferably, LIG4 or XRCC6. The heterologous DSB repair gene may comprise a nucleic acid sequence at least 70%, 75%, 80%, 85%, 90%, 95%, 96%, 97%, 98% or 99% identical to the nucleic acid sequence of SEQ ID No: 5, 6, 7 or 8. The heterologous DSB repair gene may comprise the nucleic acid sequence of SEQ ID No: 5, 6, 7 or 8. The heterologous DSB repair gene may consist of the nucleic acid sequence of SEQ ID No: 5, 6, 7 or 8.

According to the production method, the heterologous nucleic acid sequence encoding the recombinant product of interest may be integrated into the genome of the recombinant eukaryotic cell. The recombinant product of interest may be a protein or polypeptide. The recombinant product of interest may be an antibody, for example, a polyclonal antibody, a monoclonal antibody, a chimeric antibody, CDR-grafted antibody or humanized antibody. In one embodiment, the recombinant product of interest may be a monoclonal antibody. The eukaryotic cells may further comprise a heterologous nucleic acid sequence encoding a selection marker. The heterologous nucleic acid sequence encoding the selection marker may be integrated into the genome of the recombinant eukaryotic cell.

According to the production method of the present invention, the productivity of the recombinant product of interest by the eukaryotic cells may drop less than 5%, 10%, 15%, 18%, 20%, 25%, 30%, 35%, 40%, 45%, 50%, 55%, 60%, 65% or 70% over a period. The period may be at least 1, 2, 3, 4, 5, 6 or 7 weeks, 1 month, or 1, 2, 5, 10, 20, 30, 40, 50, or 60 population doublings of the cell culture. The period may be no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture. The period may be 1-10, 1-30, or 1-60 days from the start of cultivation of the cells. For example, the productivity of the recombinant product of interest by the eukaryotic cells may drop less than 30% over 8 weeks or less than 18% over a period of at least 11 weeks.

According to the production method of the present invention, the eukaryotic cells may retain at least 30%, 35%, 40%, 45%, 50%, 55%, 60%, 65%, 70%, 75%, 80%, 85%, 90% or 95% of the copy number of the heterologous nucleic acid sequence encoding the recombinant product of interest over a period. The period may be at least 1, 2, 3, 4, 5, 6 or 7 weeks, 1 month, or 1, 2, 5, 10, 20, 30, 40, 50, or 60 population doublings of the cell culture. The period may be no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture. The period may be 1-10, 1-30, or 1-60 days from the start of cultivation of the cells. In one embodiment, the eukaryotic cells may retain at least 70% of the copy number of the heterologous nucleic acid sequence encoding the recombinant product of interest over a period of at least 8 weeks. In another embodiment, the eukaryotic cells may retain at least 75% of the copy number of the heterologous nucleic acid sequence encoding the recombinant product of interest over a period of at least 11 weeks.

A method of improving production of a recombinant product of interest by eukaryotic cells (improvement method) is provided. The eukaryotic cells comprise a heterologous nucleic acid sequence encoding the recombinant product of interest and produce the recombinant product of interest. The method comprises expressing a heterologous double strand break (DSB) repair protein by the recombinant eukaryotic cells. The method may further comprise enhancing DSB repair in the eukaryotic cells. The method may further comprise enhancing stability of the eukaryotic cells over a period. The period may be at least 1, 2, 3, 4, 5, 6 or 7 weeks, 1 month, or 1, 2, 5, 10, 20, 30, 40, 50, or 60 population doublings of the cell culture. The period may be no more than 8, 9, 10, 11, 12, 15, 18 or 24 weeks, 2, 3, 4, 5, 6, 7, 8, 9, 10, 11, 12, 15, 18 or 24 months, or 70, 80, 90, 100, 110, 120, 130, 140, or 150 population doublings of the cell culture. The period may be 1-10, 1-30, or 1-60 days from the start of cultivation of the cells. The method may further comprise growing the eukaryotic cells under a condition that induces DNA damage.

According to the improvement method, the heterologous DSB repair protein may be expressed transiently or stably, preferably stably, in the eukaryotic cells. The eukaryotic cells may be mammalian cells. The mammalian cells may be selected from the group consisting of rodent cells, mouse cells and Chinese hamster cells. The mammalian cells may be CHO cells. The heterologous DSB repair protein may be from a Chinese hamster (CH) cell. The heterologous DSB repair protein may be from a Chinese hamster ovary (CHO) cell. The heterologous DSB repair protein may be LIG4, XRCC6, PALB2 or PARI, preferably, LIG4 or XRCC6. The heterologous DSB repair protein may comprise an amino acid sequence at least 70%, 75%, 80%, 85%, 90%, 95%, 96%, 97%, 98% or 99% identical to the amino acid sequence of SEQ ID No: 1, 2, 3 or 4. The heterologous DSB repair protein may comprise the amino acid sequence of SEQ ID No: 1, 2, 3 or 4. The heterologous DSB repair protein may consist of the amino acid sequence of SEQ ID No: 1, 2, 3 or 4. The eukaryotic cells may comprise a heterologous nucleic acid sequence encoding the heterologous DSB repair protein. The heterologous DSB repair gene may be integrated into the genome of the eukaryotic cell. The heterologous DSB repair gene may encode LIG4, XRCC6, PALB2 or PARI, preferably, LIG4 or XRCC6. The heterologous DSB repair gene may comprise a nucleic acid sequence at least 70%, 75%, 80%, 85%, 90%, 95%, 96%, 97%, 98% or 99% identical to the nucleic acid sequence of SEQ ID No: 5, 6, 7 or 8. The heterologous DSB repair gene may comprise the nucleic acid sequence of SEQ ID No: 5, 6, 7 or 8. The heterologous DSB repair gene may consist of the nucleic acid sequence of SEQ ID No: 5, 6, 7 or 8.

According to the improvement method, the heterologous nucleic acid sequence encoding the recombinant product of interest may be integrated into the genome of the recombinant eukaryotic cell. The recombinant product of interest may be a protein or polypeptide. The recombinant product of interest may be an antibody, for example, a polyclonal antibody, a monoclonal antibody, a chimeric antibody, CDR-grafted antibody or humanized antibody. In one embodiment, the recombinant product of interest may be a monoclonal antibody. The eukaryotic cells may further comprise a heterologous nucleic acid sequence encoding a selection marker. The heterologous nucleic acid sequence encoding the selection marker may be integrated into the genome of the recombinant eukaryotic cell.

A method of investigating suitability of eukaryotic cells as host cells for producing a recombinant product of interest (investigation method) is provided. The eukaryotic cells comprise a heterologous nucleic acid sequence encoding the recombinant product of interest. The method comprises expressing a heterologous double strand break (DSB) repair protein by the eukaryotic cells; and determining DSB repair in the eukaryotic cells. An improvement of the DSB repair indicates that the eukaryotic cells are suitable as host cells for producing a recombinant product of interest. The method may further comprise quantifying the expression of the heterologous double strand break (DSB) repair protein, for example, LIG4 or XRCC6, in the eukaryotic cells. The method may further comprise quantifying the expression of the recombinant product of interest by the eukaryotic cells. The method may further comprise identifying eukaryotic cells into whose genome the heterologous nucleic acid sequence encoding the recombinant product of interest is integrated, and optionally identifying eukaryotic cells producing the recombinant product of interest in an amount greater than 1, 10, 50, 100, 150, 200, 250 or 500 mg per liter for recombinant eukaryotic cells. The method may further comprise growing the eukaryotic cells under a condition that induces DNA damage.

According to the investigation method, the heterologous DSB repair protein may be expressed transiently or stably, preferably stably, in the eukaryotic cells. The eukaryotic cells may be mammalian cells. The mammalian cells may be selected from the group consisting of rodent cells, mouse cells and Chinese hamster cells. The mammalian cells may be CHO cells. The heterologous DSB repair protein may be from a Chinese hamster (CH) cell. The heterologous DSB repair protein may be LIG4, XRCC6, PALB2 or PARI, preferably, LIG4 or XRCC6. The heterologous DSB repair protein may comprise an amino acid sequence at least 70%, 75%, 80%, 85%, 90%, 95%, 96%, 97%, 98% or 99% identical to the amino acid sequence of SEQ ID No: 1, 2, 3 or 4. The heterologous DSB repair protein may comprise the amino acid sequence of SEQ ID No: 1, 2, 3 or 4. The heterologous DSB repair protein may consist of the amino acid sequence of SEQ ID No: 1, 2, 3 or 4. The eukaryotic cells may comprise a heterologous nucleic acid sequence encoding the heterologous DSB repair protein. The heterologous DSB repair gene may be integrated into the genome of the eukaryotic cell. The heterologous DSB repair gene may encode LIG4, XRCC6, PALB2 or PARI, preferably, LIG4 or XRCC6. The heterologous DSB repair gene may comprise a nucleic acid sequence at least 70%, 75%, 80%, 85%, 90%, 95%, 96%, 97%, 98% or 99% identical to the nucleic acid sequence of SEQ ID No: 5, 6, 7 or 8. The heterologous DSB repair gene may comprise the nucleic acid sequence of SEQ ID No: 5, 6, 7 or 8. The heterologous DSB repair gene may consist of the nucleic acid sequence of SEQ ID No: 5, 6, 7 or 8.

According to the investigation method, the heterologous nucleic acid sequence encoding the recombinant product of interest may be integrated into the genome of the recombinant eukaryotic cell. The recombinant product of interest may be a protein or polypeptide. The recombinant product of interest may be an antibody, for example, a polyclonal antibody, a monoclonal antibody, a chimeric antibody, CDR-grafted antibody or humanized antibody. In one embodiment, the recombinant product of interest may be a monoclonal antibody. The eukaryotic cells may further comprise a heterologous nucleic acid sequence encoding a selection marker. The heterologous nucleic acid sequence encoding the selection marker may be integrated into the genome of the recombinant eukaryotic cell.

Example 1. Rescue of Deficient DNA Double-Strand Break Repair in CHO Cells

Materials and Methods

Plasmid Construction

To clone eight DSB repair genes, total mRNA from CHO-K1 cells or Chinese hamster liver tissue was extracted using Qiagen RNeasy Mini kit and reverse-transcribed into cDNA to be used as templates to generate gene fragments by PCR. All primers used for cloning are listed in Table 1. FBXO18 gene and partial sequences of RNF8 and LIG4 genes were synthesized as gBlocks Gene Fragments (Integrated DNA Technologies, Coralville, Iowa). A vector fragment was obtained by PCR amplification from plasmid pcDNA3.1/zeo(+) (Thermo Fisher, Waltham, Mass.). Plasmids expressing DSB repair genes were constructed via Gibson assembly of gene fragment(s) and the vector fragment following the manufacturer's instruction (New England Biolabs, Ipswich, Mass.).

TABLE 1

Oligonucleotides used for gene cloning

| Cloning primers | Oligonucleotide sequence (5' to 3') | SEQ ID NO |
|---|---|---|
| XRCC5 F1 | GGAGACCCAAGCTGGCTAGCCCAGCAACATGGCGTGGT | 9 |
| XRCC5 R1 | CGCCGTAGACTCTCACTGAAGGAG | 10 |
| XRCC5 F2 | GAGATCTACTCCTTCAGTGAGAGT | 11 |
| XRCC5 R2 | GGTTTAACGGGCCCTCTAGACTATATCATATCCAGTAAATCATCCACATCG | 12 |
| XRCC6 F | GGAGACCCAAGCTGGCTAGCAAACCAACATGTCAGGGTGG | 13 |
| XRCC6 R | GGTTTAACGGGCCCTCTAGATCAGTTCTTATGAAGTGTCTG | 14 |
| RNF8 F | TGTCTCCCTGCCTTGCCTTA | 15 |
| RNF8 R | GTTTAAACGGGCCCTCTAGATCATGACAGTCTCTTTGCTT | 16 |
| LIG4 F | GGAGACCCAAGCTGGCTAGCTTGCTTCTATGGCTACCTCA | 17 |

TABLE 1-continued

Oligonucleotides used for gene cloning

| Cloning primers | Oligonucleotide sequence (5' to 3') | SEQ ID NO |
|---|---|---|
| LIG4 R | GCCTGGATTCTGCACTATAT | 18 |
| PALB2 F1 | GGAGACCCAAGCTGGCTAGCCCATCCGGATGGAAGAGCCT | 19 |
| PALB2 R1 | GACATATGACGGGTAGTTCTAACGTAGTATTCTGCAGGAAACG | 20 |
| PALB2 F2 | ATACTACGTTAGAACTACCCGTCATATGTCAGACTATC | 21 |
| PALB2 R2 | GGTTTAACGGGCCCTCTAGATTAAAAGTAGCGGTATATGAATATATTTC | 22 |
| PARI F | GGAGACCCAAGCTGGCTAGCCTAGGAGAATGGCTGTGCTC | 23 |
| PARI R | GTTTAAACGGGCCCTCTAGATCACAGCCTAAAAACTGAG | 24 |
| MUS81 F | GGAGACCCAAGCTGGCTAGCTAGATCTTATGGCGGCACGG | 25 |
| MUS81 R | GTTTAAACGGGCCCTCTAGATCAGGTCAGTGGACTGTGGC | 26 |
| pcDNA3.1 F | TCTAGAGGGCCCGTTTAAAC | 27 |
| pcDNA3.1 R | GCTAGCCAGCTTGGGTCTCC | 28 |

Cell Culture and Transfection

CHO-K1, BHK-21 hamster fibroblast (ATCC, Manassas, Va.) and bEnd.3 mouse endothelial cells (ATCC, Manassas, Va.) were cultured in 5 mL Iscove's Modified Dulbecco's Medium (IMDM, Hyclone Laboratories Inc., Logan, Utah) supplemented with 10% fetal bovine serum (FBS, Hyclone Laboratories Inc., Logan, Utah) in T-25 culture flasks (Corning Inc., Corning, N.Y.) at 37° C. and 5%/0 $CO_2$. For the transient expression of DSB repair genes in CHO-K1, $6 \times 10^6$ cells were transfected with 6 µg plasmid (unless indicated otherwise) using the Nucleofector Kit T (Lonza, Cologne, Germany).

Immunofluorescence

CHO-K1, bEnd.3 or transfected CHO-K1 cells were seeded in chambers of an 8-well chambered cover glass (Cellvis, Mountain View, Calif.) at $2 \times 10^5$ cells/mL with 0.5 mL culture media. After 24-hour incubation, cells were treated with 10 µg/mL bleomycin (Sigma-Aldrich, St. Louis, Mo.) for 1 or 12 hours or with 50 µg/mL for 1 hour, followed by immediate media change with fresh warm culture media. After indicated hours of incubation in fresh media, the treated cells were washed three times with Tris buffered saline (TBS), fixed with 4% paraformaldehyde in TBS for 15 min, washed three times with TBS, permeabilized with 0.1% Triton-X100 (Sigma-Aldrich, St. Louis, Mo.) in TBS for 5 min, and washed three times with TBS. Cells were then blocked in TBS containing 3% goat serum (Sigma-Aldrich, St. Louis, Mo.) for 1 hour, incubated with 1:500 primary antibody (anti-phosphorylated γH2AX antibody, EMD Millipore, Billerica, Mass.) at 4° C. overnight, washed three times with TBS, and incubated with 1:1000 Alexa Fluor 488-conjugated secondary antibody (anti-mouse IgG antibody, Life Technologies, Carlsbad, Calif.) for 1 hour at room temperature. After three TBS washes, nuclei were stained with 4',6-diamidino-2-phenylindole (DAPI, Invitrogen, Carlsbad, Calif.) for 15 min and again washed three times with TBS. Images were taken using a LSM 710 confocal microscope (Carl Zeiss, Thornwood, N.Y.) with a 63× objective. At least 50 cells and foci were counted per cell sample in duplicate cultures using software ImageJ.

Viability of Cells Post DSB Induction

Cells were treated with or without 10 µg/mL bleomycin (Sigma-Aldrich, St. Louis, Mo.) for 12 hours, followed by immediate media change with fresh warm culture media. Viable cells were counted daily up to four days post DSB induction. The survival rate was calculated as the viable cells in the treatment sample divided by those in the non-treatment control sample.

Results

CHO Cells are Deficient in DSB Repair

To test our hypothesis that the DSB repair system is not functioning effectively in CHO cells, DSB repair was compared between three cell lines, CHO-K1, BHK-21 and bEnd.3. To eliminate possible differential impacts of external culture environment on DSB formation and repair, the three cells were maintained in the same culture media and incubation conditions, and always treated in the same manner during experiments. An endogenous DSB level was first estimated by counting the number of γH2AX foci per cell in more than 100 cells. While CHO cells had an average of 0.7 DSBs more than bEnd.3 cells, the difference was not significant (p-value=0.20, Student's t-test), as both cells exhibited a similar level of endogenous DSBs, with ~4.4 DSB formation per cell (FIG. 1A). BHK-21 cells had a lower endogenous DSB level than CHO-K1 and bEND.3 cells, with only 1.7 DSB formation per cell.

The DSB repair of the three cells was then compared by calculating the rate of decrease in γH2AX foci number following DSB induction with one-hour treatment of 10 or 50 µg/mL bleomycin (BL). As expected, the higher concentration of bleomycin added to the media induced more DSBs in cells (FIGS. 1B and 1C, and Table 2). However, CHO cells had substantially fewer DSBs after bleomycin treatment under both conditions, and also showed a slower repair rate than both BHK-21 and bEnd.3 cells, repairing fewer induced DSBs per hour (Table 2). Two possibilities are consistent with these observations. Either CHO cells have a lower DSB repair rate than BHK-21 and bEnd.3 cells in general, or the increase in DSBs in BHK-21 and bEnd.3 cells trigger a higher DSB repair rate.

TABLE 2

DSB repair

| | BL (µg/mL) | Induced DSB number | Repair rate (DSB/hour) |
|---|---|---|---|
| CHO-K1 | 10 | 6 | 0.9 |
| BHK-21 | 10 | 13 | 1.8 |
| bEnd.3 | 10 | 14 | 2.2 |
| CHO-K1 | 50 | 13 | 1.7 |
| BHK-21 | 50 | 20 | 2.3 |
| bEnd.3 | 50 | 21 | 3.2 |

Figure 2:
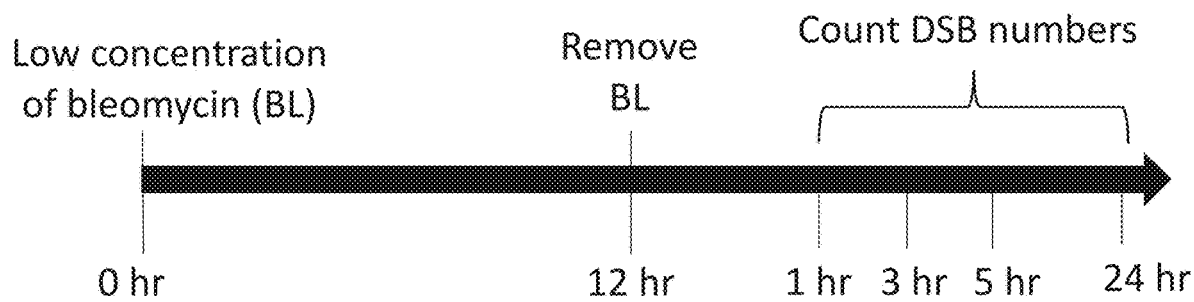
FIG. 2 shows (A) a graphical illustration of the experimental process. (B) Remaining average DSB numbers in CHO-K1, BHK-21 and bEnd.3 cells after 12-hour treatment with 10 μg/mL bleomycin. On the scatter plot, the 95% confidence interval is drawn for the mean DSB number at the given time point.
Figure 2:
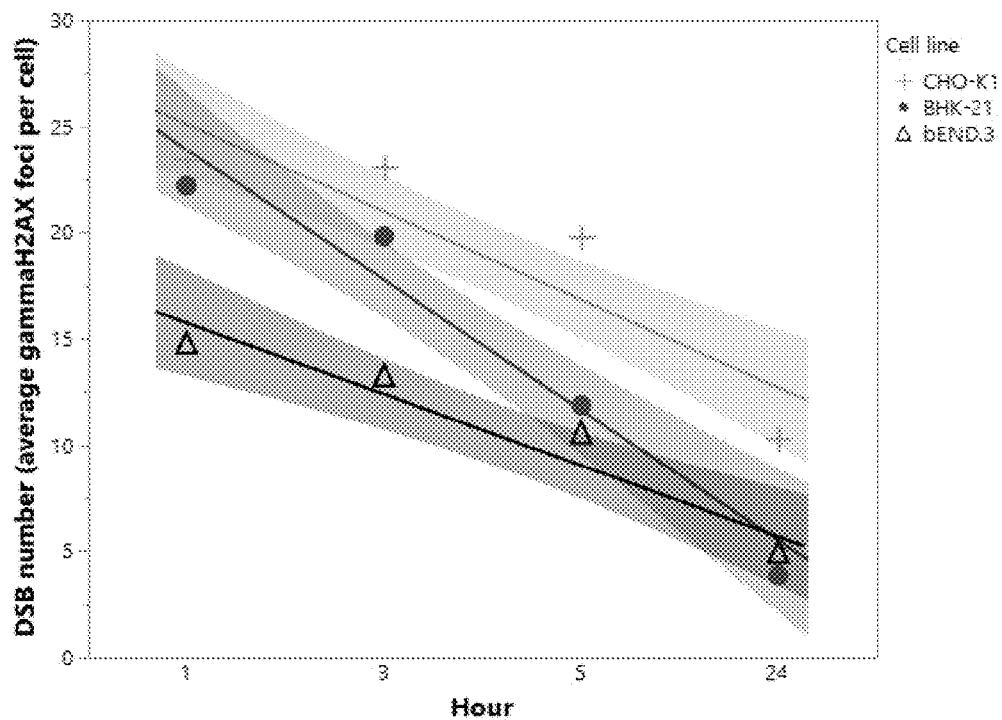

A more appropriate comparison of repair efficiency requires an equivalent level of induced DSB formation in all cell lines. With an equivalent level of induced DSBs, the observed difference in the rate of DSB disappearance is governed by the repair capability of each cell line, and thus can more accurately reflect the difference of DSB repair between different cell types. However, the number of induced DSBs is proportional to the intracellular concentration of bleomycin, and the transport mechanism of bleomycin possibly varies between different cell lines. Without a detailed understanding of the transport rates of bleomycin in CHO, BHK-21 and bEnd.3 cells, a one-hour treatment may not be sufficient to allow bleomycin to reach the same intracellular level in cells. Alternatively, given sufficient treatment time, passive diffusion of bleomycin through any cellular membrane will reach equilibrium, thus producing the same amount of intracellular bleomycin and subsequently, the same number of DSBs. Therefore, a 12-hour treatment was tested with 10 μg/mL bleomycin. Induction and repair of DSBs happen simultaneously during the 12 hours, and the cell with a slow repair would exhibit more DSBs after bleomycin removal (FIG. 2A). Indeed, because of slower repair, the CHO cells had more DSBs than bEnd.3 cells (FIG. 2B). After removing bleomycin, the CHO cells continued to repair DSBs at a rate of 0.89 DSB per hour, significantly lower than the rate of 1.03 DSB per hour by the bEnd.3 cells (p-value=$2.06 \times 10^{-10}$, ANCOVA analysis). CHO and BHK-21 cells had similar DSBs remaining after the 12-hour treatment. However, after bleomycin removal, BHK-21 cells exhibited a much higher repair rate, 2.64 DSB per hour (add statistical analysis). The results of comparing DSB repair under three conditions were all consistent with the hypothesis that DSB repair is deficient in CHO cells.

Expression of CH-Version Genes Improved DSB Repair

Figure 3:
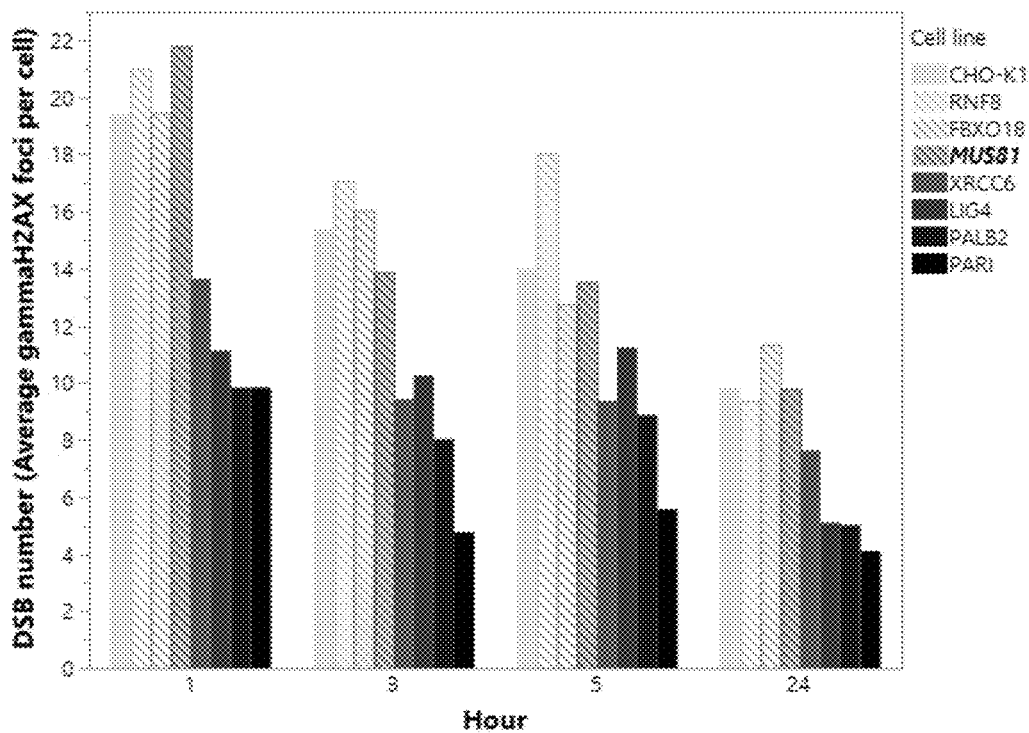
FIG. 3 shows DSB numbers in CHO-K1 cells with or without expression of CH-version DSB repair genes at various hours after bleomycin treatment. The CHO-K1 cells were transfected with null vector plasmid or plasmids expressing the indicated CH-version genes. Cells were incubated with 10 μg/mL bleomycin for 12 hours. Each error bar is constructed using a 95% confidence interval of the mean.

By comparing CHO-K1 and CH genome sequences, seven DSB repair genes were found to have notable sequence deviations between CHO and CH cells (Table 3), suggesting that these genes might be defective genes that result in a lower efficiency of the DSB repair system of CHO cells. To test the effect of gene sequence deviations on the repair capability, the seven DSB repair genes of functional (CH) versions were cloned, and transiently expressed individually in CHO cells. A 12-hour treatment with 10 μg/mL bleomycin was used to induce DSBs. After bleomycin removal, the number of γH2AX foci was quantified at four time points to evaluate DSB repair in the CHO cells expressing the CH-version genes. At one hour after bleomycin removal, a large number of DSBs were still unrepaired in control CHO-K1 cells (FIG. 3), whereas four CH-version genes helped the cells to achieve a lower DSB level (LIG4, PALB2, XRCC6 and PARI). In addition, the CHO cells managed to repair a certain amount of DSBs within 24 hours after bleomycin removal, but the four CH-version genes led to further reduced DSB numbers and significantly improved DSB repair. This result suggests that the sequence variations in the four DSB repair genes might be associated with the deficient DSB repair system of CHO cells, and expressing functional CH-version genes can improve DSB repair.

TABLE 3

CHO-version DSB genes: sequence variations compared to CH-version

| Repair Pathway | Function | Gene | Nucleotide Change | Amino Acid Change |
| --- | --- | --- | --- | --- |
| HDR | Core Repair Machinery | PALB2 | 941 T > G  1190 C > T | I314S  T397I |
|  | Regulator of HDR Execution | PARI | 161 G > A | G54E |
|  |  | FBXO18 | 25 C > T | L9F |
|  |  | MUS81 | 346 C > A  971 C > G | L116M  T324R |
| NHEJ | Upstream Regulator | RNF8 | 138 base pair deletion | 46 amino acid deletion |
|  | Core Repair | XRCC6 | 1818 G > T | Q606H |

TABLE 3-continued

CHO-version DSB genes: sequence variations compared to CH-version

| Repair Pathway | Function | Gene | Nucleotide Change | Amino Acid Change |
| --- | --- | --- | --- | --- |
|  | Machinery | LIG4 | 433 C > A  2221T > C | L145I  C741R |

Figure 4:
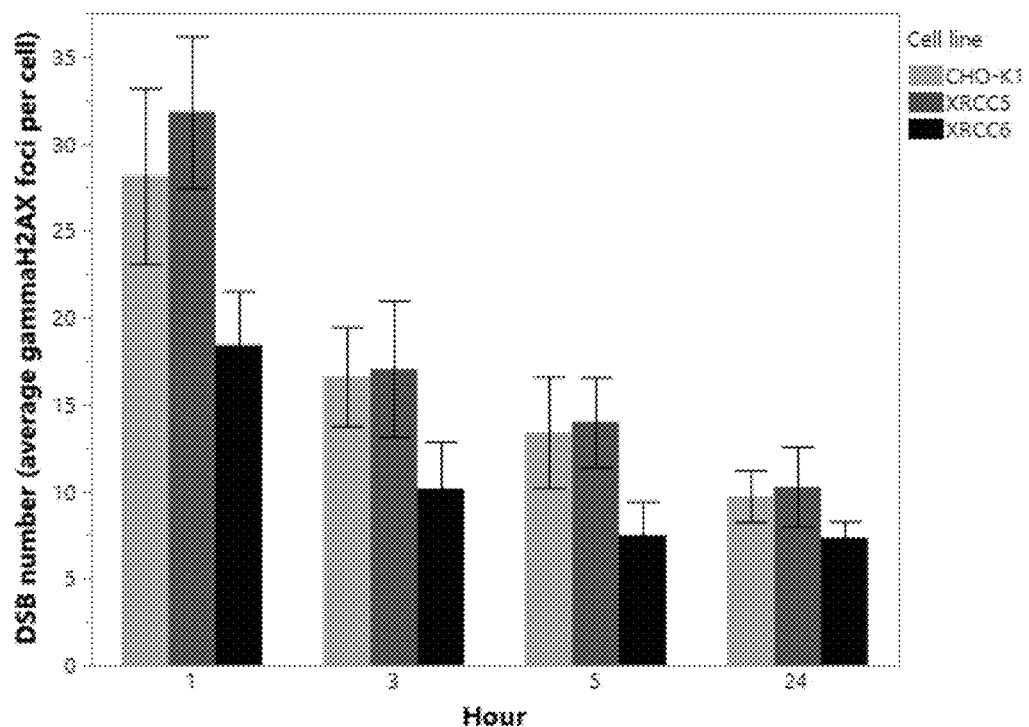
FIG. 4 shows number of remaining DSBs in CHO-K1 cells expressing the CH-version of XRCC6 or XRCC5 after bleomycin treatment. The control CHO-K1 cells were transfected with null vector plasmid. All cells were treated with 10 μg/mL bleomycin for 12 hours. Each error bar is constructed using a 95% confidence interval of the mean.

The significant positive impact of CH-version XRCC6 on CHO's DSB repair leads to a question about its partner, the CH-version XRCC5. To participate in the NHEJ pathway, XRCC6 needs to form a heterodimer (called Ku) with XRCC5 to rapidly recognize DSBs and bind DNA ends with high affinity. Ku also activates DNA-dependent protein kinase and serves as a scaffold to recruit other key components in the NHEJ pathway. Unexpectedly, the expression of CH-version XRCC5 did not improve the repair in CHO cells (FIG. 4). These observations may suggest that the XRCC6 unit, rather than XRCC5 in Ku, is the defective component, impairing NHEJ pathway and undermining the DSB repair capability in CHO cells.

Overexpression of Specific DSB Repair Genes can Improve DSB Repair

Figure 5:
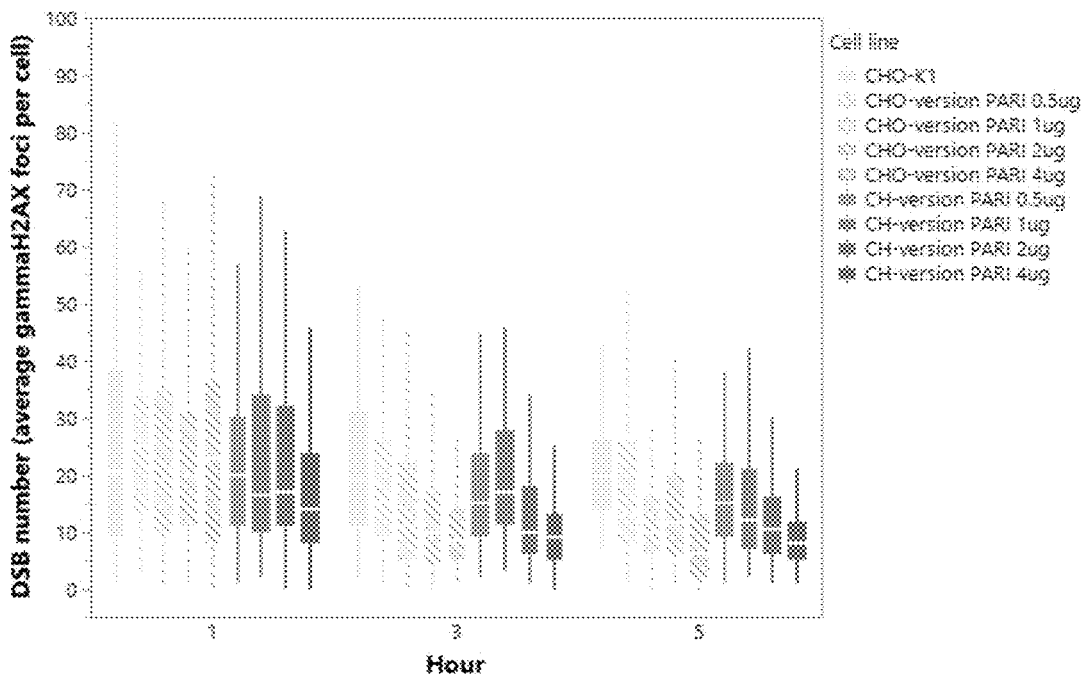
FIG. 5 shows the effect of four DSB genes expression levels on DSB repair. CHO-K1 cells were transfected with the null vector plasmid, or with the indicated amount of the plasmid expressing the CH or CHO-version PARI (A), XRCC6 (B), LIG4 (C) and PALB2 (D). All transfections were made with four million cells. The cells were treated with 10 μg/mL bleomycin for 12 hours. Each error bar is constructed using a 95% confidence interval of the mean.
Figure 5:
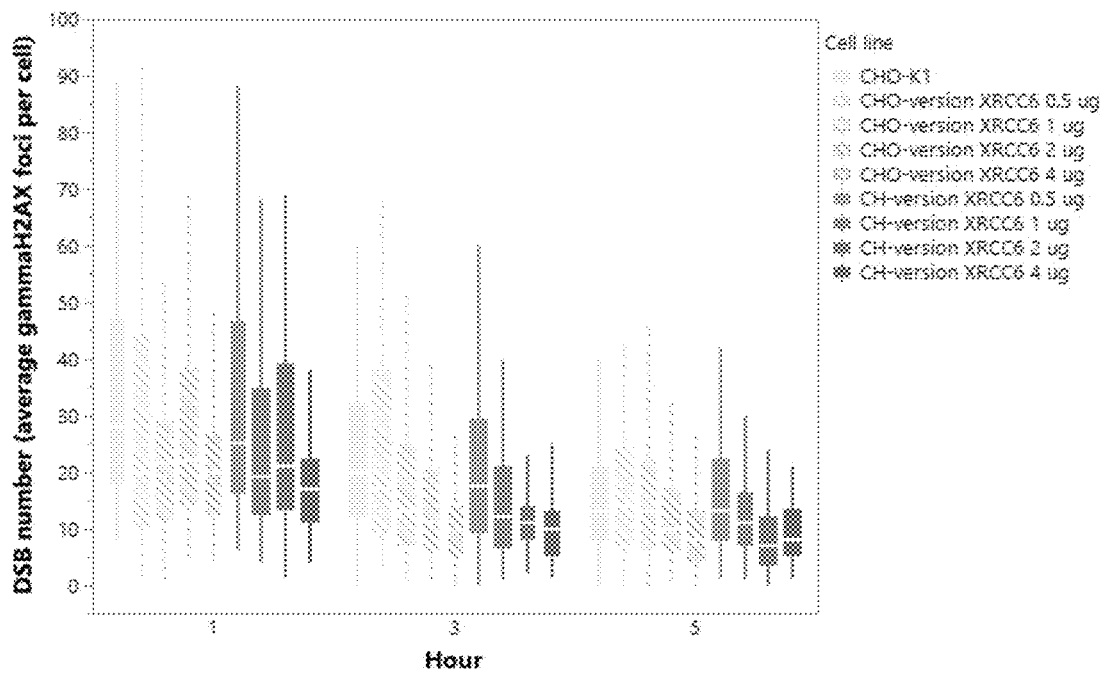
Figure 5:
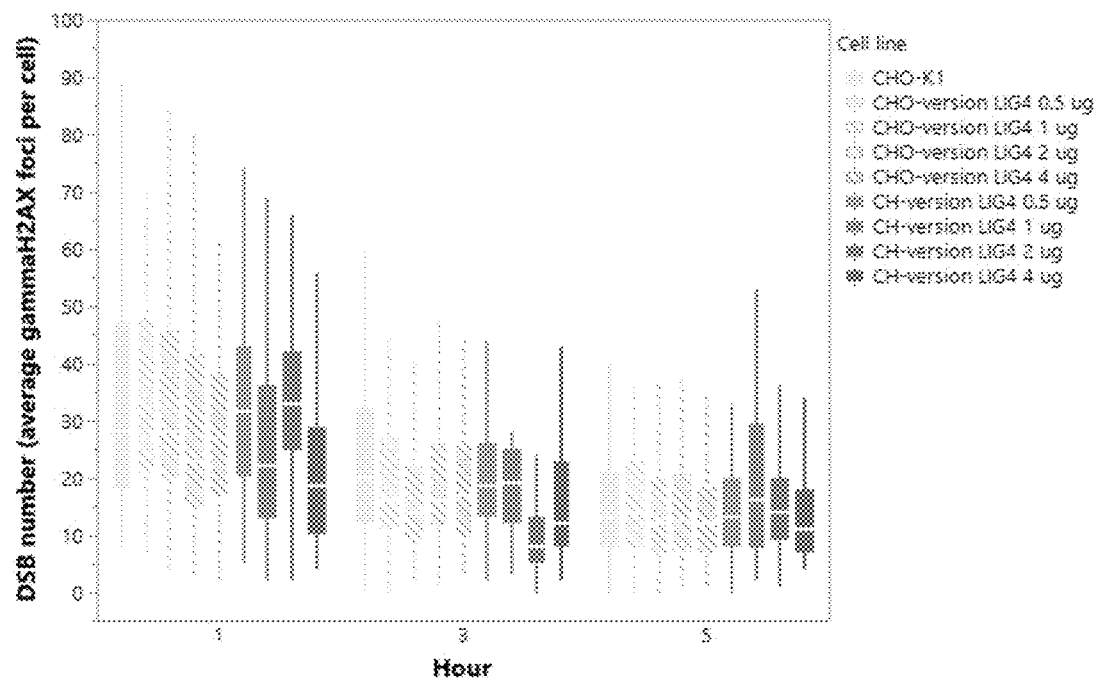
Figure 5:
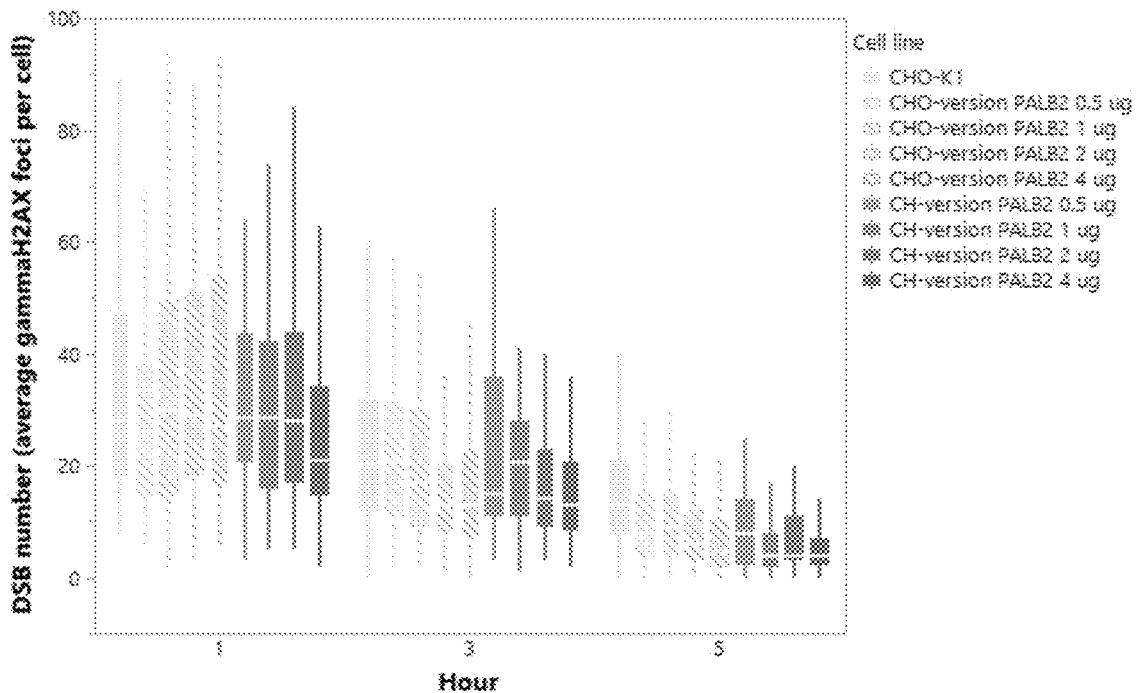

Two possible underlying mechanisms may be resulting in the observed improvement in repair by expressing the four CH-version DSB repair genes: a) the sequence differences in the four CHO-version genes impair protein function and expression of the correct CH-version rescues the DSB repair pathway; or b) CHO-version genes are functioning adequately and the heterologous expression of the CH genes simply provides copies of functioning proteins that increase the repair rate. To address this question, the four repair genes, PALB2, PARI, LIG4, and XRCC6 were cloned with their corresponding CHO-version sequences. The effect of CH or CHO-version genes on repair capability was compared in CHO cells transfected with the two versions of expression plasmids. The relationship between gene abundance and DSB repair was also explored by transfecting various concentrations of plasmid. For all four of the genes tested, cells expressing the CH-version did not seem to provide a significant improvement in DSB repair compared with the cells expressing the CHO-version of genes, at any given time point (FIG. 5). This observations is consistent with CHO-version genes functioning adequately relative to CH-version genes where the overexpression of the CHO-version would produce similar impacts on DSB repair improvement as the CH-counterparts. Another interesting observation is that the DSB repair efficiency changed in a concentration dependent manner in cells expressing XRCC6 or PARI (FIGS. 5A and B), but not PALB2 or LIG4 (FIGS. 5C and D). As the expression of XRCC6 or PARI increased, CHO cells showed fewer DSBs remaining and thus had a better DSB repair. These results are consistent with a mechanism where the improvement in DSB repair by expressing CH- or CHO-version DSB genes is primarily due to an increased abundance of the respective proteins.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A recombinant mammalian cell expressing a heterologous double strand break (DSB) repair protein in an amount effective for enhancing DSB repair in the cell, wherein the heterologous DSB repair protein is selected from the group consisting of DNA ligase IV (LIG4), X-ray repair cross complementing 6 (XRCC6), partner and localizer of BRCA2 (PALB2), and PARP1 binding protein which is encoded by the PARPBP gene (PARI).

2. The recombinant mammalian cell of claim 1, wherein the heterologous DSB repair protein is expressed in an amount effective for enhancing stability of the cell for at least 1 month.

3. The recombinant mammalian cell of claim 1, wherein the heterologous DSB repair protein is LIG4 or XRCC6.

4. The recombinant mammalian cell of claim 1, wherein the heterologous DSB repair protein is expressed transiently.

5. The recombinant mammalian cell of claim 1, wherein the heterologous DSB repair protein is expressed stably.

6. The recombinant mammalian cell of claim 1, wherein the mammalian cell is selected from the group consisting of a rodent cell, a mouse cell and a Chinese hamster cell.

7. The recombinant mammalian cell of claim 1, wherein the mammalian cell is a Chinese hamster ovary (CHO) cell.

8. The recombinant mammalian cell of claim 1, wherein the heterologous DSB repair protein is from a Chinese hamster cell.

9. The recombinant mammalian cell of claim 1, wherein the heterologous DSB repair protein is from a Chinese hamster ovary (CHO) cell.

10. The recombinant mammalian cell of claim 1, wherein the heterologous DSB repair protein comprises an amino acid sequence at least 70% identical to the amino acid sequence of SEQ ID NO: 1, 2, 3 or 4.

11. The recombinant mammalian cell of claim 1, wherein the recombinant mammalian cell comprises a heterologous DSB repair gene encoding the heterologous DSB repair protein.

12. The recombinant mammalian cell of claim 11, wherein the heterologous DSB repair gene comprises a nucleic acid sequence at least 70% identical to the nucleic acid sequence of SEQ ID NO: 5, 6, 7 or 8.

13. A method for enhancing double strand break (DSB) repair in the recombinant mammalian cells of claim 1, comprising expressing an effective amount of a heterologous DSB repair protein in the mammalian cells.

14. A method for establishing the recombinant mammalian cells of claim 1 as host cells for production of a recombinant product of interest, comprising: (a) expressing a heterologous double strand break (DSB) repair protein in the mammalian cells; (b) determining DSB repair in the mammalian cells of step (a); and (c) isolating mammalian cells in which the DSB repair is enhanced as host cells.

15. A method for producing a recombinant product of interest, comprising:
(a) growing the recombinant mammalian cells of claim 1 in a culture medium;
(b) expressing a heterologous double strand break (DSB) repair protein in the recombinant mammalian cells; and
(c) expressing the recombinant product of interest by the recombinant mammalian cells.

16. A method of improving production of a recombinant product of interest by the recombinant mammalian cells of claim 1, comprising expressing a heterologous double strand break (DSB) repair protein by the recombinant mammalian cells.

17. A method of investigating suitability of the recombinant mammalian cells of claim 1 as host cells for producing a recombinant product of interest, comprising:
(a) expressing a heterologous double strand break (DSB) repair protein by the recombinant mammalian cells; and
(b) determining DSB repair in the recombinant mammalian cells, wherein an improvement of the DSB repair indicates that the recombinant mammalian cells are suitable as host cells for producing a recombinant product of interest.

18. The host cells established according to the method of claim 14.

* * * * *

SEQUENCE LISTING

<160> NUMBER OF SEQ ID NOS: 28

<210> SEQ ID NO 1
<211> LENGTH: 912
<212> TYPE: PRT
<213> ORGANISM: Cricetulus griseus

<400> SEQUENCE: 1

```
Met Ala Thr Ser Gln Thr Ser Gln Thr Val Ala Ala His Val Pro Phe
 1               5                  10                  15

Ala Asp Leu Cys Ser Thr Leu Glu Arg Ile Gln Lys Ser Lys Glu Arg
                20                  25                  30

Ala Glu Lys Ile Arg His Phe Lys Glu Phe Leu Asp Ser Trp Arg Lys
            35                  40                  45

Phe His Asp Ala Leu His Lys Asn Lys Lys Asp Val Thr Asp Ser Phe
 50                  55                  60

Tyr Pro Ala Met Arg Leu Ile Leu Pro Gln Leu Glu Arg Glu Arg Met
 65                  70                  75                  80

Ala Tyr Gly Ile Lys Glu Thr Met Leu Ala Lys Leu Tyr Ile Glu Leu
                85                  90                  95

Leu Asn Leu Pro Arg Glu Gly Lys Asp Ala Leu Lys Leu Leu Asn Tyr
                100                 105                 110

Arg Thr Pro Ser Gly Ala Arg Thr Asp Ala Gly Asp Phe Ala Val Ile
            115                 120                 125

Ala Tyr Phe Val Leu Lys Pro Arg Cys Leu Gln Lys Gly Ser Leu Thr
130                 135                 140

Leu Gln Gln Val Asn Glu Leu Leu Asp Leu Val Ala Ser Asn Asn Ser
145                 150                 155                 160

Gly Lys Arg Lys Asp Leu Val Lys Lys Ser Leu Leu Gln Leu Ile Thr
                165                 170                 175

Gln Ser Ser Ala Leu Glu Gln Lys Trp Leu Ile Arg Met Ile Ile Lys
            180                 185                 190

Asp Leu Lys Leu Gly Val Ser Gln Gln Thr Ile Leu Asn Ile Phe His
        195                 200                 205

Asn Asp Ala Val Glu Leu His Asn Val Thr Thr Asp Leu Glu Lys Val
210                 215                 220

Cys Arg Gln Leu His Asp Pro Ala Val Gly Leu Ser Asp Ile Ser Ile
225                 230                 235                 240

Thr Leu Phe Ser Ala Phe Lys Pro Met Leu Ala Ala Val Ala Asp Val
                245                 250                 255

Glu Arg Val Glu Lys Asp Met Lys Gln Gln Ser Phe Tyr Ile Glu Thr
            260                 265                 270

Lys Leu Asp Gly Glu Arg Met Gln Met His Lys Asp Gly Ser Val Tyr
        275                 280                 285

Gln Tyr Phe Ser Arg Asn Gly Tyr Asn Tyr Thr Asp Gln Phe Gly Ala
            290                 295                 300

Ser Pro Gln Glu Gly Thr Leu Thr Pro Phe Ile His Asp Ala Phe Arg
305                 310                 315                 320

Thr Asp Val Gln Val Cys Ile Leu Asp Gly Glu Met Met Ala Tyr Asn
                325                 330                 335

Pro Thr Thr Gln Thr Phe Met Gln Lys Gly Val Lys Phe Asp Ile Lys
            340                 345                 350

Arg Met Val Glu Asp Ser Asp Leu Gln Thr Cys Tyr Cys Val Phe Asp
        355                 360                 365
```

-continued

Val Leu Met Val Asn Asn Lys Lys Leu Gly Arg Glu Thr Leu Arg Lys
370                 375                 380

Arg Tyr Asp Ile Leu Asn Ser Thr Phe Thr Pro Ile Gln Gly Arg Ile
385                 390                 395                 400

Glu Ile Val Gln Lys Lys Leu Ala Gln Thr Lys Asn Glu Val Val Asp
            405                 410                 415

Ala Leu Asn Glu Ala Ile Asp Lys Arg Glu Glu Gly Ile Met Ile Lys
            420                 425                 430

His Pro Leu Ser Ile Tyr Lys Pro Asp Lys Arg Gly Glu Gly Trp Leu
        435                 440                 445

Lys Ile Lys Pro Glu Tyr Val Ser Gly Leu Met Asp Glu Leu Asp Leu
450                 455                 460

Leu Ile Val Gly Gly Tyr Trp Gly Lys Gly Ser Arg Gly Gly Met Met
465                 470                 475                 480

Ser His Phe Leu Cys Ala Val Ala Glu Lys Pro Pro His Gly Glu Lys
                485                 490                 495

Pro Ser Val Phe His Thr Leu Cys Arg Val Gly Ser Gly Tyr Thr Met
            500                 505                 510

Lys Glu Leu Tyr Asp Leu Gly Leu Lys Leu Ala Lys Tyr Trp Lys Pro
            515                 520                 525

Phe His Lys Lys Ser Pro Pro Ser Ser Ile Leu Cys Gly Thr Glu Lys
        530                 535                 540

Pro Glu Val Tyr Ile Glu Pro Cys Asn Ser Val Ile Val Gln Ile Lys
545                 550                 555                 560

Ala Ala Glu Ile Val Pro Ser Asp Met Tyr Lys Thr Gly Thr Thr Leu
                565                 570                 575

Arg Phe Pro Arg Ile Glu Lys Ile Arg Asp Asp Lys Glu Trp His Glu
            580                 585                 590

Cys Met Thr Leu Gly Asp Leu Glu Glu Leu Arg Gly Lys Ala Ser Gly
            595                 600                 605

Lys Leu Ala Thr Lys His Leu His Val Gly Asp Asp Glu Pro Arg
        610                 615                 620

Glu Lys Arg Arg Lys Pro Val Ser Lys Met Lys Lys Thr Ile Gly Ile
625                 630                 635                 640

Ile Glu His Leu Lys Ala Pro Asn Leu Ser Asn Ile Ser Lys Val Ser
                645                 650                 655

Asn Val Phe Glu Asp Val Glu Phe Cys Val Met Ser Gly Leu Asp Gly
            660                 665                 670

Tyr Pro Lys Ser Asp Leu Glu Asn Arg Ile Ala Glu Phe Gly Gly Tyr
        675                 680                 685

Ile Val Gln Asn Pro Gly Pro Asp Thr Tyr Cys Val Ile Ala Gly Cys
690                 695                 700

Glu Asn Ile Arg Val Lys Asn Ile Ile Ser Ser Asp Gln His Asp Val
705                 710                 715                 720

Val Lys Pro Glu Trp Leu Leu Glu Cys Phe Lys Thr Lys Thr Cys Val
                725                 730                 735

Pro Trp Gln Pro Cys Phe Met Ile His Met Cys Pro Ser Thr Lys Gln
            740                 745                 750

His Phe Ala Arg Glu Tyr Asp Cys Tyr Gly Asp Ser Tyr Phe Val Asp
        755                 760                 765

Thr Asp Leu Asp Gln Leu Lys Glu Val Phe Leu Gly Ile Lys Lys Ala
770                 775                 780

Gly Glu His Gln Thr Pro Glu Glu Met Ala Pro Val Ile Ala Asp Leu

```
            785                 790                 795                 800
Glu Tyr Arg Tyr Ser Trp Asp His Ser Pro Leu Cys Met Phe Arg His
                805                 810                 815

Cys Thr Val Tyr Leu Asp Leu Tyr Ala Val Ile Asn Asp Ser Ser Ser
                820                 825                 830

Lys Ile Lys Ala Thr Arg Leu Asp Val Thr Ala Leu Glu Leu Arg Phe
                835                 840                 845

His Gly Ala Lys Val Val Ser His Leu Ser Glu Gly Val Ser His Val
                850                 855                 860

Ile Ile Gly Glu Asp Gln Ser Arg Val Ser Asp Phe Lys Val Phe Arg
865                 870                 875                 880

Arg Thr Leu Lys Lys Lys Phe Lys Ile Leu Gln Glu Arg Trp Val Thr
                885                 890                 895

Asp Ser Val Asp Lys Gly Glu Leu Gln Glu Asn Gln Tyr Leu Leu
                900                 905                 910

<210> SEQ ID NO 2
<211> LENGTH: 608
<212> TYPE: PRT
<213> ORGANISM: Cricetulus griseus

<400> SEQUENCE: 2

Met Ser Gly Trp Glu Ser Tyr Tyr Lys Thr Glu Gly Glu Glu Glu
1               5                   10                  15

Glu Glu Glu Glu Ser Pro Asp Pro Gly Gly Tyr Lys Tyr Ser Gly
                20                  25                  30

Arg Asp Ser Leu Ile Phe Leu Val Asp Ala Ser Arg Ala Met Phe Asp
                35                  40                  45

Ser Gln Gly Glu Asp Glu Val Thr Pro Phe Asp Met Ser Ile Gln Cys
50                  55                  60

Ile Gln Ser Val Tyr Thr Ser Lys Ile Ile Ser Ser Asn Arg Asp Leu
65                  70                  75                  80

Leu Gly Val Val Phe Tyr Gly Thr Glu Lys Asp Lys Asn Ser Val Asn
                85                  90                  95

Phe Lys Asn Ile Tyr Val Leu Gln Glu Leu Asp Asn Pro Gly Ala Lys
                100                 105                 110

Arg Val Leu Glu Leu Asp Gln Phe Lys Gly Gln Gln Gly Lys Lys His
                115                 120                 125

Phe Gln Asp Thr Ile Gly His Gly Ser Asp Tyr Ser Leu Ser Glu Val
                130                 135                 140

Leu Trp Val Cys Ala Asn Leu Phe Ser Asp Val Gln Val Lys Met Ser
145                 150                 155                 160

His Lys Arg Ile Met Leu Phe Thr Asn Glu Asp Asp Pro His Gly Asn
                165                 170                 175

Asp Ser Ala Lys Ala Ser Arg Ala Arg Thr Lys Ala Asn Asp Leu Arg
                180                 185                 190

Asp Thr Gly Ile Phe Leu Asp Leu Met His Leu Lys Arg Arg Gly Gly
                195                 200                 205

Phe Asp Ile Ser Leu Phe Tyr Arg Asp Ile Ile Ser Ile Ala Glu Asp
                210                 215                 220

Glu Asp Leu Gly Val His Phe Glu Glu Ser Ser Lys Leu Glu Asp Leu
225                 230                 235                 240

Leu Arg Lys Val Arg Ala Lys Glu Thr Lys Lys Arg Val Leu Ser Arg
                245                 250                 255
```

```
Leu Arg Phe Lys Leu Gly Lys Asp Val Ala Leu Met Val Gly Ile Tyr
            260                 265                 270

Asn Leu Ile Gln Lys Ala Asn Lys Pro Phe Pro Val Arg Leu Tyr Arg
            275                 280                 285

Glu Thr Asn Glu Pro Val Lys Thr Lys Thr Arg Thr Phe Asn Val Asn
        290                 295                 300

Thr Gly Ser Leu Leu Pro Ser Asp Thr Lys Arg Ser Gln Thr Tyr
305                 310                 315                 320

Gly Ser Arg Gln Ile Val Leu Glu Lys Glu Thr Glu Glu Leu Lys
                325                 330                 335

Arg Phe Asp Glu Pro Gly Leu Ile Leu Met Gly Phe Lys Pro Leu Val
            340                 345                 350

Met Leu Lys Lys His His Tyr Leu Arg Pro Ser Leu Phe Val Tyr Pro
            355                 360                 365

Glu Glu Ser Leu Val Asn Gly Ser Ser Thr Leu Phe Ser Ala Leu Leu
        370                 375                 380

Thr Lys Cys Leu Glu Lys Glu Val Met Ala Val Cys Arg Tyr Thr Ser
385                 390                 395                 400

Arg Lys Asn Val Pro Pro Tyr Phe Val Ala Leu Val Pro Gln Glu Glu
                405                 410                 415

Glu Leu Asp Asp Gln Asn Ile Gln Val Thr Pro Ala Gly Phe Gln Leu
            420                 425                 430

Val Phe Leu Pro Tyr Ala Asp Lys Arg Lys Val Pro Phe Thr Glu
                435                 440                 445

Lys Val Met Ala Asn Pro Glu Gln Ile Asp Lys Met Lys Ala Ile Val
450                 455                 460

His Lys Leu Arg Phe Thr Tyr Arg Ser Asp Ser Phe Glu Asn Pro Val
465                 470                 475                 480

Leu Gln Gln His Phe Arg Asn Leu Glu Ala Leu Ala Leu Asp Met Met
                485                 490                 495

Glu Ser Glu Gln Val Val Asp Leu Thr Leu Pro Lys Ala Glu Ala Ile
            500                 505                 510

Lys Lys Arg Leu Gly Ser Leu Ala Asp Glu Phe Lys Glu Leu Val Tyr
            515                 520                 525

Pro Pro Gly Tyr Asn Pro Glu Gly Lys Ala Thr Lys Arg Lys Gln Asp
            530                 535                 540

Asp Glu Gly Ser Ala Ser Lys Lys Pro Lys Val Glu Leu Ser Glu Glu
545                 550                 555                 560

Glu Leu Lys Ala His Phe Ala Lys Gly Thr Leu Gly Lys Leu Thr Val
                565                 570                 575

Pro Thr Leu Lys Glu Val Cys Lys Ala Tyr Gly Leu Lys Ser Gly Pro
            580                 585                 590

Lys Lys Gln Glu Leu Leu Asp Ala Leu Thr Arg His Phe Gln Lys Asn
            595                 600                 605

<210> SEQ ID NO 3
<211> LENGTH: 912
<212> TYPE: PRT
<213> ORGANISM: Cricetulus griseus

<400> SEQUENCE: 3

Met Ala Thr Ser Gln Thr Ser Gln Thr Val Ala Ala His Val Pro Phe
1               5                   10                  15

Ala Asp Leu Cys Ser Thr Leu Glu Arg Ile Gln Lys Ser Lys Glu Arg
            20                  25                  30
```

```
Ala Glu Lys Ile Arg His Phe Lys Glu Phe Leu Asp Ser Trp Arg Lys
         35                  40                  45
Phe His Asp Ala Leu His Lys Asn Lys Lys Asp Val Thr Asp Ser Phe
     50                  55                  60
Tyr Pro Ala Met Arg Leu Ile Leu Pro Gln Leu Glu Arg Glu Arg Met
 65              70                  75                  80
Ala Tyr Gly Ile Lys Glu Thr Met Leu Ala Lys Leu Tyr Ile Glu Leu
                 85                  90                  95
Leu Asn Leu Pro Arg Glu Gly Lys Asp Ala Leu Lys Leu Leu Asn Tyr
                100                 105                 110
Arg Thr Pro Ser Gly Ala Arg Thr Asp Ala Gly Asp Phe Ala Val Ile
                115                 120                 125
Ala Tyr Phe Val Leu Lys Pro Arg Cys Leu Gln Lys Gly Ser Leu Thr
            130                 135                 140
Ile Gln Gln Val Asn Glu Leu Leu Asp Leu Val Ala Ser Asn Asn Ser
145                 150                 155                 160
Gly Lys Arg Lys Asp Leu Val Lys Ser Leu Leu Gln Leu Ile Thr
                165                 170                 175
Gln Ser Ser Ala Leu Glu Gln Lys Trp Leu Ile Arg Met Ile Lys
            180                 185                 190
Asp Leu Lys Leu Gly Val Ser Gln Gln Thr Ile Leu Asn Ile Phe His
            195                 200                 205
Asn Asp Ala Val Glu Leu His Asn Val Thr Thr Asp Leu Glu Lys Val
        210                 215                 220
Cys Arg Gln Leu His Asp Pro Ala Val Gly Leu Ser Asp Ile Ser Ile
225                 230                 235                 240
Thr Leu Phe Ser Ala Phe Lys Pro Met Leu Ala Ala Val Ala Asp Val
                245                 250                 255
Glu Arg Val Glu Lys Asp Met Lys Gln Gln Ser Phe Tyr Ile Glu Thr
            260                 265                 270
Lys Leu Asp Gly Glu Arg Met Gln Met His Lys Asp Gly Ser Val Tyr
        275                 280                 285
Gln Tyr Phe Ser Arg Asn Gly Tyr Asn Tyr Thr Asp Gln Phe Gly Ala
    290                 295                 300
Ser Pro Gln Glu Gly Thr Leu Thr Pro Phe Ile His Asp Ala Phe Arg
305                 310                 315                 320
Thr Asp Val Gln Val Cys Ile Leu Asp Gly Glu Met Met Ala Tyr Asn
                325                 330                 335
Pro Thr Thr Gln Thr Phe Met Gln Lys Gly Val Lys Phe Asp Ile Lys
            340                 345                 350
Arg Met Val Glu Asp Ser Asp Leu Gln Thr Cys Tyr Cys Val Phe Asp
        355                 360                 365
Val Leu Met Val Asn Asn Lys Lys Leu Gly Arg Glu Thr Leu Arg Lys
    370                 375                 380
Arg Tyr Asp Ile Leu Asn Ser Thr Phe Thr Pro Ile Gln Gly Arg Ile
385                 390                 395                 400
Glu Ile Val Gln Lys Lys Leu Ala Gln Thr Lys Asn Glu Val Val Asp
                405                 410                 415
Ala Leu Asn Glu Ala Ile Asp Lys Arg Glu Glu Gly Ile Met Ile Lys
            420                 425                 430
His Pro Leu Ser Ile Tyr Lys Pro Asp Lys Arg Gly Glu Gly Trp Leu
        435                 440                 445
```

```
Lys Ile Lys Pro Glu Tyr Val Ser Gly Leu Met Asp Glu Leu Asp Leu
    450                 455                 460
Leu Ile Val Gly Gly Tyr Trp Gly Lys Gly Ser Arg Gly Gly Met Met
465                 470                 475                 480
Ser His Phe Leu Cys Ala Val Ala Glu Lys Pro Pro His Gly Glu Lys
                485                 490                 495
Pro Ser Val Phe His Thr Leu Cys Arg Val Gly Ser Gly Tyr Thr Met
            500                 505                 510
Lys Glu Leu Tyr Asp Leu Gly Leu Lys Leu Ala Lys Tyr Trp Lys Pro
        515                 520                 525
Phe His Lys Lys Ser Pro Pro Ser Ser Ile Leu Cys Gly Thr Glu Lys
530                 535                 540
Pro Glu Val Tyr Ile Glu Pro Cys Asn Ser Val Ile Val Gln Ile Lys
545                 550                 555                 560
Ala Ala Glu Ile Val Pro Ser Asp Met Tyr Lys Thr Gly Thr Thr Leu
                565                 570                 575
Arg Phe Pro Arg Ile Glu Lys Ile Arg Asp Asp Lys Glu Trp His Glu
            580                 585                 590
Cys Met Thr Leu Gly Asp Leu Glu Glu Leu Arg Gly Lys Ala Ser Gly
        595                 600                 605
Lys Leu Ala Thr Lys His Leu His Val Gly Asp Asp Glu Pro Arg
610                 615                 620
Glu Lys Arg Arg Lys Pro Val Ser Lys Met Lys Lys Thr Ile Gly Ile
625                 630                 635                 640
Ile Glu His Leu Lys Ala Pro Asn Leu Ser Asn Ile Ser Lys Val Ser
                645                 650                 655
Asn Val Phe Glu Asp Val Glu Phe Cys Val Met Ser Gly Leu Asp Gly
            660                 665                 670
Tyr Pro Lys Ser Asp Leu Glu Asn Arg Ile Ala Glu Phe Gly Gly Tyr
        675                 680                 685
Ile Val Gln Asn Pro Gly Pro Asp Thr Tyr Cys Val Ile Ala Gly Cys
        690                 695                 700
Glu Asn Ile Arg Val Lys Asn Ile Ile Ser Ser Asp Gln His Asp Val
705                 710                 715                 720
Val Lys Pro Glu Trp Leu Leu Glu Cys Phe Lys Thr Lys Thr Cys Val
                725                 730                 735
Pro Trp Gln Pro Arg Phe Met Ile His Met Cys Pro Ser Thr Lys Gln
            740                 745                 750
His Phe Ala Arg Glu Tyr Asp Cys Tyr Gly Asp Ser Tyr Phe Val Asp
        755                 760                 765
Thr Asp Leu Asp Gln Leu Lys Glu Val Phe Leu Gly Ile Lys Lys Ala
        770                 775                 780
Gly Glu His Gln Thr Pro Glu Glu Met Ala Pro Val Ile Ala Asp Leu
785                 790                 795                 800
Glu Tyr Arg Tyr Ser Trp Asp His Ser Pro Leu Cys Met Phe Arg His
                805                 810                 815
Cys Thr Val Tyr Leu Asp Leu Tyr Ala Val Ile Asn Asp Ser Ser Ser
            820                 825                 830
Lys Ile Lys Ala Thr Arg Leu Asp Val Thr Ala Leu Glu Leu Arg Phe
        835                 840                 845
His Gly Ala Lys Val Val Ser His Leu Ser Glu Gly Val Ser His Val
850                 855                 860
Ile Ile Gly Glu Asn Gln Ser Arg Val Ser Asp Phe Lys Val Phe Arg
```

```
                865                 870                 875                 880
Arg Thr Leu Lys Lys Lys Phe Lys Ile Leu Gln Glu Arg Trp Val Thr
                    885                 890                 895
Asp Ser Val Asp Lys Gly Glu Leu Gln Glu Glu Asn Gln Tyr Leu Leu
                    900                 905                 910

<210> SEQ ID NO 4
<211> LENGTH: 608
<212> TYPE: PRT
<213> ORGANISM: Cricetulus griseus

<400> SEQUENCE: 4

Met Ser Gly Trp Glu Ser Tyr Tyr Lys Thr Glu Gly Glu Glu Glu Glu
1               5                   10                  15
Glu Glu Glu Glu Ser Pro Asp Pro Gly Gly Tyr Lys Tyr Ser Gly
            20                  25                  30
Arg Asp Ser Leu Ile Phe Leu Val Asp Ala Ser Arg Ala Met Phe Asp
            35                  40                  45
Ser Gln Gly Glu Asp Glu Val Thr Pro Phe Asp Met Ser Ile Gln Cys
        50                  55                  60
Ile Gln Ser Val Tyr Thr Ser Lys Ile Ile Ser Ser Asn Arg Asp Leu
65                  70                  75                  80
Leu Gly Val Val Phe Tyr Gly Thr Glu Lys Asp Lys Asn Ser Val Asn
                    85                  90                  95
Phe Lys Asn Ile Tyr Val Leu Gln Glu Leu Asp Asn Pro Gly Ala Lys
                100                 105                 110
Arg Val Leu Glu Leu Asp Gln Phe Lys Gly Gln Gly Lys Lys His
            115                 120                 125
Phe Gln Asp Thr Ile Gly His Gly Ser Asp Tyr Ser Leu Ser Glu Val
            130                 135                 140
Leu Trp Val Cys Ala Asn Leu Phe Ser Asp Val Gln Val Lys Met Ser
145                 150                 155                 160
His Lys Arg Ile Met Leu Phe Thr Asn Glu Asp Asp Pro His Gly Asn
                    165                 170                 175
Asp Ser Ala Lys Ala Ser Arg Ala Arg Thr Lys Ala Asn Asp Leu Arg
                180                 185                 190
Asp Thr Gly Ile Phe Leu Asp Leu Met His Leu Lys Arg Arg Gly Gly
            195                 200                 205
Phe Asp Ile Ser Leu Phe Tyr Arg Asp Ile Ile Ser Ile Ala Glu Asp
            210                 215                 220
Glu Asp Leu Gly Val His Phe Glu Glu Ser Ser Lys Leu Glu Asp Leu
225                 230                 235                 240
Leu Arg Lys Val Arg Ala Lys Glu Thr Lys Lys Arg Val Leu Ser Arg
                    245                 250                 255
Leu Arg Phe Lys Leu Gly Lys Asp Val Ala Leu Met Val Gly Ile Tyr
                    260                 265                 270
Asn Leu Ile Gln Lys Ala Asn Lys Pro Phe Pro Val Arg Leu Tyr Arg
                275                 280                 285
Glu Thr Asn Glu Pro Val Lys Thr Lys Thr Arg Thr Phe Asn Val Asn
            290                 295                 300
Thr Gly Ser Leu Leu Leu Pro Ser Asp Thr Lys Arg Ser Gln Thr Tyr
305                 310                 315                 320
Gly Ser Arg Gln Ile Val Leu Glu Lys Glu Glu Thr Glu Glu Leu Lys
                    325                 330                 335
```

```
Arg Phe Asp Glu Pro Gly Leu Ile Leu Met Gly Phe Lys Pro Leu Val
                340                 345                 350

Met Leu Lys Lys His His Tyr Leu Arg Pro Ser Leu Phe Val Tyr Pro
            355                 360                 365

Glu Glu Ser Leu Val Asn Gly Ser Ser Thr Leu Phe Ser Ala Leu Leu
        370                 375                 380

Thr Lys Cys Leu Glu Lys Glu Val Met Ala Val Cys Arg Tyr Thr Ser
385                 390                 395                 400

Arg Lys Asn Val Pro Pro Tyr Phe Val Ala Leu Val Pro Gln Glu Glu
                405                 410                 415

Glu Leu Asp Asp Gln Asn Ile Gln Val Thr Pro Ala Gly Phe Gln Leu
            420                 425                 430

Val Phe Leu Pro Tyr Ala Asp Asp Lys Arg Lys Val Pro Phe Thr Glu
        435                 440                 445

Lys Val Met Ala Asn Pro Glu Gln Ile Asp Lys Met Lys Ala Ile Val
450                 455                 460

His Lys Leu Arg Phe Thr Tyr Arg Ser Asp Ser Phe Glu Asn Pro Val
465                 470                 475                 480

Leu Gln Gln His Phe Arg Asn Leu Glu Ala Leu Ala Leu Asp Met Met
                485                 490                 495

Glu Ser Glu Gln Val Val Asp Leu Thr Leu Pro Lys Ala Glu Ala Ile
            500                 505                 510

Lys Lys Arg Leu Gly Ser Leu Ala Asp Glu Phe Lys Glu Leu Val Tyr
        515                 520                 525

Pro Pro Gly Tyr Asn Pro Glu Gly Lys Ala Thr Lys Arg Lys Gln Asp
    530                 535                 540

Asp Glu Gly Ser Ala Ser Lys Lys Pro Lys Val Glu Leu Ser Glu Glu
545                 550                 555                 560

Glu Leu Lys Ala His Phe Ala Lys Gly Thr Leu Gly Lys Leu Thr Val
                565                 570                 575

Pro Thr Leu Lys Glu Val Cys Lys Ala Tyr Gly Leu Lys Ser Gly Pro
            580                 585                 590

Lys Lys Gln Glu Leu Leu Asp Ala Leu Thr Arg His Phe His Lys Asn
        595                 600                 605

<210> SEQ ID NO 5
<211> LENGTH: 2739
<212> TYPE: DNA
<213> ORGANISM: Cricetulus griseus

<400> SEQUENCE: 5
atggctacct cacaaacttc acaaactgtt gcagctcatg tccccttgc ggatttatgt      60 tccacattag aacgaataca gaaagtaaa gaacgtgcag aaaagatcag gcactttaag    120 gaattttag attcttggag aaaatttcat gatgcccttc ataagaacaa gaaagatgtt    180
acagactctt tttacccagc aatgagactt attcttcctc agttagaaag agagaggatg    240
gcttatggaa tcaaagaaac catgcttgct aagctttaca ttgaattgct gaatttacca    300
agagaaggca aggatgccct gaagctcctg aattatcgaa cacctagtgg agctcgcacg    360
gatgctgggg actttgcagt gatcgcatac ttcgttttga agccaaggtg cttacagaaa    420
ggaagcttaa ctctacagca ggtaaatgaa ctcttagact tagtcgccag caataattct    480
ggcaaaagaa aagacctagt gaaaagagc ctccttcagt taataaccca gagttcagcc    540
cttgagcaaa aatggctgat tcgtatgatt attaaggact tgaagcttgg tgtcagtcaa    600
```

```
caaactatac ttaacatttt tcataatgat gcagttgagt tgcacaacgt caccacagac    660
ctggaaaagg tctgtaggca gctacacgac cccgctgtag ggctcagtga tatctctatc    720
actctgtttt ctgcctttaa gccaatgctt gctgctgtag cagatgtgga acgcgtggag    780
aaggacatga agcagcagag tttctacatc gaaaccaagc tggacgggga acgcatgcag    840
atgcacaaag atgggtcggt gtatcagtac ttctccagaa acggctataa ctacactgat    900
cagtttggtg catctccaca ggaaggcact ctcaccccat tcattcatga tgcgttccgg    960
acagacgtgc aagtatgcat cctcgatggt gagatgatgg cctacaaccc gaccacacag   1020
actttcatgc aaaagggggt caaatttgat atcaaaagga tggtggaaga ttccgaccta   1080
cagacatgtt actgtgtttt tgatgtgttg atggttaata ataagaagct agggcgtgag   1140
actctgagaa agaggtatga tatccttaat agtacttttta cacccatcca aggtcgaata   1200
gaaatagtac agaaaaagct agctcagacg aagaacgaag tagtagatgc attaaacgaa   1260
gccatagata agagagaaga aggcatcatg atcaaacacc ctctgtccat ctacaagcca   1320
gacaaaagag gtgaagggtg gctaaaaatt aaaccagagt atgtcagtgg attaatggat   1380
gaattagacc tcctaattgt gggggggctac tgggggaaag gttcacgagg tggcatgatg   1440
tctcactttt tgtgtgcagt ggcagagaag cccccctcatg gtgagaagcc atctgtattc   1500
catactctgt gtcgtgttgg gtcgggatac accatgaaag aactctatga tcttggcttg   1560
aaattggcca aatactggaa gccctttcat aagaaatccc caccgagtag tattttatgt   1620
ggaacagaga agccggaagt ctacattgag ccctgtaact ctgttattgt tcagattaag   1680
gcagcagaga ttgtccccag tgacatgtac aagaccggca ccaccttgcg cttcccacgt   1740
atcgagaaga tcagagatga caaagagtgg catgaatgca tgactctggg tgacttagaa   1800
gagctgaggg ggaaagcatc tgggaaactt gccacaaaac accttcacgt aggtgacgat   1860
gatgaaccta gagaaagag gcggaaacct gtctccaaaa tgaagaaaac cattggaatt   1920
attgaacact tgaaagcgcc taaccttttct aacataagca aagtttccaa tgtatttgaa   1980
gatgttgagt tttgtgttat gagtgggttg gatggttatc ccaagtctga cctggagaac   2040
agaattgcag aatttggtgg ttatatagtg cagaatccag gcccagacac atactgtgtg   2100
attgcaggct gtgagaacat aagagtgaaa acattatct cttcagatca acatgatgtt   2160
gtcaagcctg agtggctttt agagtgtttt aaaacaaaaa cgtgtgtgcc atggcaaccc   2220
tgctttatga ttcacatgtg cccatcaaca aagcagcatt tgcccgtga atatgattgc   2280 tatggcgata gctattttgt tgatacagat ttggatcaac tgaaagaagt gtttttagga   2340
attaagaaag caggtgagca tcagactccg gaagagatgg cccctgtgat tgctgaccta   2400
gaatatcgtt attcttggga ccactctcct ctctgtatgt ttcgacactg cactgtttat   2460
ctggacctgt atgctgttat taatgactcg agttccaaaa tcaaagcaac gaggttagat   2520
gtgacagcac ttgagctgcg gtttcatgga gccaaggtag tgtcccactt atctgagggg   2580
gtatctcatg taatcatcgg ggaagatcag agccgagttt cggacttcaa agttttcaga   2640
agaactctta agaagaagtt taagatcctt caagaacgtt gggtgactga ttcagtagac   2700
aagggtgaac tacaggagga aaaccagtat ttgctttag                          2739

<210> SEQ ID NO 6
<211> LENGTH: 1827
<212> TYPE: DNA
<213> ORGANISM: Cricetulus griseus

<400> SEQUENCE: 6
```

```
atgtcagggt gggaatccta ctacaaaacc gagggtgagg aagaggaaga agaggaggag    60
agccctgacc caggtggaga atataaatat tcaggaagag atagtttgat ttttctggtt   120
gatgcctcca gggctatgtt tgactctcag ggtgaagatg aagttacacc ttttgatatg   180
agcatccagt gtatccagag tgtgtacacc agtaagatca taagcagcaa ccgagatctc   240
ttgggagtgg tgttctatgg taccgagaaa gacaaaaact cagtgaattt caaaaatatt   300
tatgtcttac aagagttgga taacccaggt gctaaacgtg tgctagagct tgaccagttt   360
aagggacaac agggaaaaaa acatttccaa gacacaattg ccatggatc tgattactcc    420 ttaagtgaag tgctctgggt ctgtgccaac ctcttcagtg acgtccaggt caagatgagt   480
cacaagagga tcatgctctt cacaaatgaa gatgatccac atggcaatga cagtgccaaa   540
gccagccggg ccaggaccaa agctaatgat ctccgtgaca ctgggatctt ccttgacttg   600
atgcatctga agagacgagg gggctttgac atatccttgt tctacagaga catcatcagc   660
atagctgagg atgaggatct cggggttcac tttgaggaat caagcaagct ggaagacctg   720
ctaaggaagg ttcgcgccaa ggaaaccaaa aagcgagtac tgtccaggtt aaggtttaag   780
cttggtaaag acgtagcact catggtgggc atctataact tgatccagaa agctaacaag   840
ccttttccag tgaggctcta tcgagaaaca atgaaccag tgaaaaccaa gactaggact    900
tttaatgtaa acacgggcag tctgctcctg cctagtgata ccaaacggtc tcagacctat   960
gggagtcgtc aaattgtgct agagaaagag gaaacagagg agctgaagcg gtttgatgag  1020
ccgggtttga tccttatggg ctttaagccc ttggtaatgc tgaagaagca ccactacctg  1080
aggccttccc tgtttgtgta cccagaggag tccctggtaa acgggagctc aaccttgttc  1140
agtgctctgc tcaccaagtg tctggagaag gaggtcatgg cagtgtgtag atacacatcc  1200
cgaaagaacg tgcccccta ttttgtggct ttggtgccac aggaagagga actggatgat   1260
cagaatattc aggtgacgcc agcaggcttc agcttgtct tcctccccta tgctgatgac   1320
aagcggaagg tgcccttta ctgagaaagtg atggccaacc cgagcagat agacaagatg    1380 aaagctattg ttcataagct tcgctttaca tacaggagtg acagttttga gaatccagtg  1440
ctgcagcagc acttccggaa cctggaggcc ttgctttgg atatgatgga gtctgagcaa   1500
gtggtagatc tgacactgcc caaggctgaa gccataaaga aaagactggg ctccctggct  1560
gatgagttta agagcttgt ctaccccct gggtataatc tgagggaaa agctaccaag     1620 agaaaacaag atgatgaagg ttctgcaagt aaaaagccca aggtagagtt atcagaagaa  1680
gagctgaagg cccattttgc caagggcaca ctgggcaagc taactgtgcc tacactaaag  1740
gaggtctgta aggcctatgg gcttaagagt ggaccgaaga agcaggaact gctagatgct  1800
ctcaccagac acttccagaa gaactga                                      1827

<210> SEQ ID NO 7
<211> LENGTH: 2739
<212> TYPE: DNA
<213> ORGANISM: Cricetulus griseus

<400> SEQUENCE: 7
atggctacct cacaaacttc acaaactgtt gcagctcatg tcccctttgc ggatttatgt    60
tccacattag aacgaataca gaaaagtaaa gaacgtgcag aaaagatcag gcactttaag   120
gaatttttag attcttggag aaaatttcat gatgccttc ataagaacaa gaaagatgtt    180
acagactctt tttacccagc aatgagactt attcttcctc agttagaaag agagaggatg   240
```

```
gcttatggaa tcaaagaaac catgcttgct aagctttaca ttgaattgct gaatttacca    300
agagaaggca aggatgccct gaagctcctg aattatcgaa cacctagtgg agctcgcacg    360
gatgctgggg actttgcagt gatcgcatac ttcgttttga agccaaggtg cttacagaaa    420
ggaagcttaa ctatacagca ggtaaatgaa ctcttagact tagtcgccag caataattct    480
ggcaaaagaa aagacctagt gaaaaagagc ctccttcagt taataaccca gagttcagcc    540
cttgagcaaa aatggctgat tcgtatgatt attaaggact tgaagcttgg tgtcagtcaa    600
caaactatac ttaacatttt tcataatgat gcagttgagt tgcacaacgt caccacagac    660
ctggaaaagg tctgtaggca gctacacgac cccgctgtag ggctcagtga tatctctatc    720
actctgtttt ctgcctttaa gccaatgctc gctgctgtag cagatgtgga acgcgtggag    780
aaggacatga agcagcagag tttctacatc gaaaccaagc tggacgggga acgcatgcag    840
atgcacaaag atgggtcggt gtatcagtac ttctccagaa atggctataa ctacactgat    900
cagtttggtg catctccaca ggaaggcact ctcaccccat tcattcatga tgcgttccgg    960
acagacgtgc aagtatgcat cctcgatggt gagatgatgg cctacaaccc gaccacacag   1020
actttcatgc aaaaggggt caaatttgat atcaaaagga tggtggaaga ttccgaccta   1080
cagacatgtt actgtgtttt tgatgtgttg atggttaata taagaagct agggcgtgag   1140
actctgagaa agaggtatga tatccttaat agtacttta cacccatcca aggtcgaata   1200
gaaatagtac agaaaaagct agctcagacg aagaacgaag tagtagatgc attaaacgaa   1260
gccatagata agagagaaga gggcatcatg atcaaacacc ctctgtccat ctacaagcca   1320
gacaaaagag gtgaagggtg gctaaaaatt aaaccagagt atgtcagtgg attaatggat   1380
gaattagacc tcctaattgt gggggctac tgggggaaag gttcacgagg tggcatgatg   1440
tctcactttt tgtgtgcagt ggcagagaag cccctcatg tgagaagcc atctgtattc   1500
catactctgt gtcgtgttgg gtcgggatac accatgaaag aactctatga tcttggcttg   1560
aaattggcca aatactggaa gccctttcat aagaaatccc caccgagtag tattttatgt   1620
ggaacagaga agccggaagt ctacattgag ccctgtaact ctgttattgt tcagattaag   1680
gcagcagaga ttgtccccag tgacatgtac aagaccggca ccaccttgcg cttcccacgt   1740
atcgagaaga tcagagatga caaagagtgg catgaatgca tgactctggg tgacttagaa   1800
gagctgaggg ggaaagcatc tgggaaactt gccacaaaac accttcacgt aggtgacgat   1860
gatgaaccta gagaaaagag gcggaaacct gtctccaaaa tgaagaaaac cattggaatt   1920
attgaacact tgaaagcgcc taaccttct aacataagca aagtttccaa tgtatttgaa   1980
gatgttgagt tttgtgttat gagtgggttg atggttatc ccaagtctga cctggagaac   2040
agaattgcag aatttggtgg ttatatagtg cagaatccag gcccagacac atactgtgtg   2100
attgcaggct gtgagaacat aagagtgaaa acattatct cttcagatca acatgatgtt   2160
gtcaagcctg agtggctttt agagtgtttt aaaacaaaaa cgtgtgtgcc atggcaaccc   2220
cgctttatga ttcacatgtg cccatcaaca aagcagcatt tgcccgtga atatgattgc   2280
tatggcgata gctattttgt tgatacagat ttggatcaac tgaaagaagt gtttttagga   2340
attaagaaag caggtgagca tcagactccg gaagagatgg ccctgtgat tgctgaccta   2400
gaatatcgtt attcttggga ccactctcct ctctgtatgt tcgacactg cactgtttat   2460
ctggacctgt atgctgttat taatgactcg agttccaaaa tcaaagcaac gaggttagat   2520
gtgacagcac ttgagctgcg gtttcatgga gccaaggtag tgtcccactt atctgagggg   2580
gtatctcatg taatcatcgg ggaaaatcag agccgagttt cggacttcaa agttttcaga   2640
```

| agaactctta | agaagaagtt | taagatcctt | caagaacgtt | gggtgactga | ttcagtagac | 2700 |
| aagggtgaac | tacaggagga | aaaccagtat | ttgctttag | | | 2739 |

<210> SEQ ID NO 8
<211> LENGTH: 1827
<212> TYPE: DNA
<213> ORGANISM: Cricetulus griseus

<400> SEQUENCE: 8

| atgtcagggt | gggaatccta | ctacaaaacc | gagggtgagg | aagaggaaga | agaggaggag | 60 |
| agccctgacc | caggtggaga | atataaatat | tcaggaagag | atagtttgat | ttttctggtt | 120 |
| gatgcctcca | gggctatgtt | tgactctcag | ggtgaagatg | aagttacacc | ttttgatatg | 180 |
| agcatccagt | gtatccagag | tgtgtacacc | agtaagatca | taagcagcaa | ccagatctc | 240 |
| ttgggagtgg | tgttctatgg | taccgagaaa | gacaaaaact | cagtgaattt | caaaaatatt | 300 |
| tatgtcttac | aagagttgga | taacccaggt | gctaaacgtg | tgctagagct | tgaccagttt | 360 |
| aagggacaac | agggaaaaaa | acatttccaa | gacacaattg | gccatggatc | tgattactcc | 420 |
| ttaagtgaag | tgctctgggt | ctgtgccaac | ctcttcagtg | acgtccaggt | caagatgagt | 480 |
| cacaagagga | tcatgctctt | cacaaatgaa | gatgatccac | atggcaatga | cagtgccaaa | 540 |
| gccagccggg | ccaggaccaa | agctaatgat | ctccgtgaca | ctgggatctt | ccttgacttg | 600 |
| atgcatctga | agagacgagg | gggctttgac | atatccttgt | tctacagaga | catcatcagc | 660 |
| atagctgagg | atgaggatct | cggggttcac | tttgaggaat | caagcaagct | ggaagacctg | 720 |
| ctaaggaagg | ttcgcgccaa | ggaaaccaaa | aagcgagtac | tgtccaggtt | aaggtttaag | 780 |
| cttggtaaag | acgtagcact | catggtgggc | atctataact | tgatccagaa | agctaacaag | 840 |
| ccttttccag | tgaggctcta | tcgagaaaca | aatgaaccag | tgaaaaccaa | gactaggact | 900 |
| tttaatgtaa | acacgggcag | tctgctcctg | cctagtgata | ccaaacggtc | tcagacctat | 960 |
| gggagtcgtc | aaattgtgct | agagaaagag | gaaacagagg | agctgaagcg | gtttgatgag | 1020 |
| ccgggtttga | tccttatggg | ctttaagccc | ttggtaatgc | tgaagaagca | ccactacctg | 1080 |
| aggccttccc | tgtttgtgta | cccagaggag | tccctggtaa | acgggagctc | aaccttgttc | 1140 |
| agtgctctgc | tcaccaagtg | tctggagaag | gaggtcatgg | cagtgtgtag | atacacatcc | 1200 |
| cgaaagaacg | tgccccctta | ttttgtggct | ttggtgccac | aggaagagga | actgatgat | 1260 |
| cagaatattc | aggtgacgcc | agcaggcttc | cagcttgtct | tcctccccta | tgctgatgac | 1320 |
| aagcggaagg | tgccctttac | tgagaaagtg | atggccaacc | ccgagcagat | agacaagatg | 1380 |
| aaagctattg | ttcataagct | tcgctttaca | tacaggagtg | acagttttga | gaatccagtg | 1440 |
| ctgcagcagc | acttccggaa | cctgaggcc | cttgctttgg | atatgatgga | gtctgagcaa | 1500 |
| gtggtagatc | tgacactgcc | caaggctgaa | gccataaaga | aaagactggg | ctccctggct | 1560 |
| gatgagttta | aagagcttgt | ctaccccct | gggtataatc | tgagggaaa | agctaccaag | 1620 |
| agaaaacaag | atgatgaagg | ttctgcaagt | aaaaagccca | aggtagagtt | atcagaagaa | 1680 |
| gagctgaagg | cccatttgc | caagggcaca | ctgggcaagc | taactgtgcc | tacactaaag | 1740 |
| gaggtctgta | aggcctatgg | gcttaagagt | ggaccgaaga | agcaggaact | gctagatgct | 1800 |
| ctcaccagac | acttccataa | gaactga | | | | 1827 |

<210> SEQ ID NO 9
<211> LENGTH: 38
<212> TYPE: DNA

```
<213> ORGANISM: Artificial Sequence
<220> FEATURE:
<223> OTHER INFORMATION: Synthetic

<400> SEQUENCE: 9
ggagacccaa gctggctagc ccagcaacat ggcgtggt                              38

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
cgccgtagac tctcactgaa ggag                                             24

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
gagatctact ccttcagtga gagt                                             24

<210> SEQ ID NO 12
<211> LENGTH: 51
<212> TYPE: DNA
<213> ORGANISM: Artificial Sequence
<220> FEATURE:
<223> OTHER INFORMATION: Synthetic

<400> SEQUENCE: 12
ggtttaacgg gccctctaga ctatatcata tccagtaaat catccacatc g               51

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
ggagacccaa gctggctagc aaaccaacat gtcagggtgg                            40

<210> SEQ ID NO 14
<211> LENGTH: 42
<212> TYPE: DNA
<213> ORGANISM: Artificial Sequence
<220> FEATURE:
<223> OTHER INFORMATION: Synthetic

<400> SEQUENCE: 14
ggtttaacgg gccctctaga tcagttctta tggaagtgtc tg                         42

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tgtctccctg ccttgcctta                                                  20
```

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
gtttaaacgg gccctctaga tcatgacagt ctctttgctt        40

<210> SEQ ID NO 17
<211> LENGTH: 40
<212> TYPE: DNA
<213> ORGANISM: Artificial Sequence
<220> FEATURE:
<223> OTHER INFORMATION: Synthetic

<400> SEQUENCE: 17
ggagacccaa gctggctagc ttgcttctat ggctacctca        40

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gcctggattc tgcactatat        20

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19
ggagacccaa gctggctagc ccatccggat ggaagagcct        40

<210> SEQ ID NO 20
<211> LENGTH: 43
<212> TYPE: DNA
<213> ORGANISM: Artificial Sequence
<220> FEATURE:
<223> OTHER INFORMATION: Synthetic

<400> SEQUENCE: 20
gacatatgac gggtagttct aacgtagtat tctgcaggaa acg        43

<210> SEQ ID NO 21
<211> LENGTH: 38
<212> TYPE: DNA
<213> ORGANISM: Artificial Sequence
<220> FEATURE:
<223> OTHER INFORMATION: Synthetic

<400> SEQUENCE: 21
atactacgtt agaactaccc gtcatatgtc agactatc        38

<210> SEQ ID NO 22
<211> LENGTH: 49
<212> TYPE: DNA
<213> ORGANISM: Artificial Sequence
<220> FEATURE:

<223> OTHER INFORMATION: Synthetic

<400> SEQUENCE: 22
ggtttaacgg gccctctaga ttaaaagtag cggtatatga atatatttc            49

<210> SEQ ID NO 23
<211> LENGTH: 40
<212> TYPE: DNA
<213> ORGANISM: Artificial Sequence
<220> FEATURE:
<223> OTHER INFORMATION: Synthetic

<400> SEQUENCE: 23
ggagacccaa gctggctagc ctaggagaat ggctgtgctc                      40

<210> SEQ ID NO 24
<211> LENGTH: 40
<212> TYPE: DNA
<213> ORGANISM: Artificial Sequence
<220> FEATURE:
<223> OTHER INFORMATION: Synthetic

<400> SEQUENCE: 24
gtttaaacgg gccctctaga tcacagccta aaaaactgag                      40

<210> SEQ ID NO 25
<211> LENGTH: 40
<212> TYPE: DNA
<213> ORGANISM: Artificial Sequence
<220> FEATURE:
<223> OTHER INFORMATION: Synthetic

<400> SEQUENCE: 25
ggagacccaa gctggctagc tagatcttat ggcggcacgg                      40

<210> SEQ ID NO 26
<211> LENGTH: 40
<212> TYPE: DNA
<213> ORGANISM: Artificial Sequence
<220> FEATURE:
<223> OTHER INFORMATION: Synthetic

<400> SEQUENCE: 26
gtttaaacgg gccctctaga tcaggtcagt ggactgtggc                      40

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
tctagagggc ccgtttaaac                                            20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gctagccagc ttgggtctcc                                            20